US012186510B2

(12) United States Patent
Keren

(10) Patent No.: US 12,186,510 B2
(45) Date of Patent: *Jan. 7, 2025

(54) TEMPORARY INTERATRIAL SHUNTS

(71) Applicants: The Medical Research, Infrastructure And Health Services Fund Of The Tel-Aviv Medical Center, Tel Aviv (IL); V-Wave Ltd., Caesarea (IL)

(72) Inventor: Gad Keren, Kiryat Ono (IL)

(73) Assignees: The Medical Research, Infrastructure and Health Services Fund of the Tel-Aviv Medical Center, Tel Aviv (IL); V-Wave Ltd., Caesarea (IL)

( * ) Notice: Subject to any disclaimer, the term of this patent is extended or adjusted under 35 U.S.C. 154(b) by 980 days.

This patent is subject to a terminal disclaimer.

(21) Appl. No.: 17/192,612

(22) Filed: Mar. 4, 2021

(65) Prior Publication Data

US 2021/0187258 A1 Jun. 24, 2021

Related U.S. Application Data

(62) Division of application No. 15/570,752, filed as application No. PCT/IB2016/052561 on May 5, 2016, now Pat. No. 10,940,296.

(Continued)

(51) Int. Cl.
*A61M 27/00* (2006.01)
*A61B 17/11* (2006.01)
(Continued)

(52) U.S. Cl.
CPC ........... *A61M 27/002* (2013.01); *A61B 17/11* (2013.01); *A61B 2017/00243* (2013.01);
(Continued)

(58) Field of Classification Search
CPC ............... A61M 27/002; A61M 25/09; A61M 2205/3344; A61B 17/11;
(Continued)

(56) References Cited

U.S. PATENT DOCUMENTS 3,852,334 A 12/1974 Dusza et al.
3,874,388 A 4/1975 King et al.
(Continued)

FOREIGN PATENT DOCUMENTS

AU 2003291117 B2 4/2009
CA 2378920 A1 2/2001
(Continued)

OTHER PUBLICATIONS

Abraham et al., "Hemodynamic Monitoring in Advanced Heart Failure: Results from the LAPTOP-HF Trial," J Card Failure, 22:940 (2016) (Abstract Only).
(Continued)

*Primary Examiner* — Philip R Wiest
(74) *Attorney, Agent, or Firm* — Greenberg Traurig, LLP; Christopher C. Bolten; Albert K. Heng

(57) ABSTRACT

Described embodiments include apparatus (28) that includes a shunt (26). The shunt includes a flared distal portion (40), a flared proximal portion (44), and an intermediate portion (42), disposed between the distal portion and the proximal portion. The apparatus further includes a constricting flexible longitudinal element (38) passing circumferentially along the intermediate portion of the shunt, configured to constrict the intermediate portion of the shunt, and one or more proximal-portion-collapsing flexible longitudinal elements (36) configured to collapse the proximal portion of the shunt. Other embodiments are also described.

20 Claims, 6 Drawing Sheets

Related U.S. Application Data

(60) Provisional application No. 62/158,022, filed on May 7, 2015.

(51) Int. Cl.
    *A61B 17/00*     (2006.01)
    *A61F 2/95*     (2013.01)
    *A61M 25/09*     (2006.01)

(52) U.S. Cl.
    CPC ............... *A61B 2017/1107* (2013.01); *A61B 2017/1139* (2013.01); *A61F 2002/9511* (2013.01); *A61F 2250/0059* (2013.01); *A61M 25/09* (2013.01); *A61M 2205/3344* (2013.01); *A61M 2210/125* (2013.01)

(58) Field of Classification Search
    CPC .. A61B 2017/00243; A61B 2017/1107; A61B 2017/1139; A61F 2002/9511
    See application file for complete search history.

(56) References Cited

U.S. PATENT DOCUMENTS

| | | |
|---|---|---|
| 3,952,334 A | 4/1976 | Bokros et al. |
| 4,364,395 A | 12/1982 | Redmond et al. |
| 4,484,955 A | 11/1984 | Hochstein |
| 4,601,309 A | 7/1986 | Chang |
| 4,617,932 A | 10/1986 | Kornberg |
| 4,662,355 A | 5/1987 | Pieronne et al. |
| 4,665,906 A | 5/1987 | Jervis |
| 4,705,507 A | 11/1987 | Boyles |
| 4,836,204 A | 6/1989 | Landymore et al. |
| 4,979,955 A | 12/1990 | Smith |
| 4,988,339 A | 1/1991 | Vadher |
| 4,995,857 A | 2/1991 | Arnold |
| 5,035,702 A | 7/1991 | Taheri |
| 5,035,706 A | 7/1991 | Giantureo et al. |
| 5,037,427 A | 8/1991 | Harada et al. |
| 5,089,005 A | 2/1992 | Harada |
| 5,186,431 A | 2/1993 | Tamari |
| 5,197,978 A | 3/1993 | Hess |
| 5,234,447 A | 8/1993 | Kaster et al. |
| 5,267,940 A | 12/1993 | Moulder |
| 5,290,227 A | 3/1994 | Pasque |
| 5,312,341 A | 5/1994 | Turi |
| 5,326,374 A | 7/1994 | Ilbawi et al. |
| 5,332,402 A | 7/1994 | Teitelbaum |
| 5,334,217 A | 8/1994 | Das |
| 5,378,239 A | 1/1995 | Termin et al. |
| 5,409,019 A | 4/1995 | Wilk |
| 5,429,144 A | 7/1995 | Wilk |
| 5,500,015 A | 3/1996 | Deac |
| 5,531,759 A | 7/1996 | Kensey et al. |
| 5,545,210 A | 8/1996 | Hess et al. |
| 5,556,386 A | 9/1996 | Todd |
| 5,578,008 A | 11/1996 | Hara |
| 5,584,803 A | 12/1996 | Stevens et al. |
| 5,597,377 A | 1/1997 | Aldea |
| 5,645,559 A | 7/1997 | Hachtman et al. |
| 5,655,548 A | 8/1997 | Nelson et al. |
| 5,662,711 A | 9/1997 | Douglas |
| 5,702,412 A | 12/1997 | Popov et al. |
| 5,725,552 A | 3/1998 | Kotula et al. |
| 5,741,324 A | 4/1998 | Glastra |
| 5,749,880 A | 5/1998 | Banas et al. |
| 5,779,716 A | 7/1998 | Cano et al. |
| 5,795,307 A | 8/1998 | Krueger |
| 5,810,836 A | 9/1998 | Hussein et al. |
| 5,824,062 A | 10/1998 | Patke et al. |
| 5,824,071 A | 10/1998 | Nelson et al. |
| 5,846,261 A | 12/1998 | Kotula et al. |
| 5,910,144 A | 6/1999 | Hayashi |
| 5,916,193 A | 6/1999 | Stevens et al. |
| 5,941,850 A | 8/1999 | Shah et al. |
| 5,957,949 A | 9/1999 | Leonhardt et al. |
| 5,990,379 A | 11/1999 | Gregory |
| 6,007,544 A | 12/1999 | Kim |
| 6,027,518 A | 2/2000 | Gaber |
| 6,039,755 A | 3/2000 | Edwin et al. |
| 6,039,759 A | 3/2000 | Carpentier et al. |
| 6,086,610 A | 7/2000 | Duerig et al. |
| 6,111,520 A | 8/2000 | Allen et al. |
| 6,117,159 A | 9/2000 | Huebsch et al. |
| 6,120,534 A | 9/2000 | Ruiz |
| 6,124,523 A | 9/2000 | Banas et al. |
| 6,126,686 A | 10/2000 | Badylak et al. |
| 6,165,188 A | 12/2000 | Saadat et al. |
| 6,210,318 B1 | 4/2001 | Lederman |
| 6,214,029 B1 | 4/2001 | Thill et al. |
| 6,214,039 B1 | 4/2001 | Banas et al. |
| 6,217,541 B1 | 4/2001 | Yu |
| 6,221,096 B1 | 4/2001 | Aiba et al. |
| 6,231,587 B1 | 5/2001 | Makower |
| 6,242,762 B1 | 6/2001 | Brown et al. |
| 6,245,099 B1 | 6/2001 | Edwin et al. |
| 6,254,564 B1 | 7/2001 | Wilk et al. |
| 6,260,552 B1 | 7/2001 | Mortier et al. |
| 6,264,684 B1 | 7/2001 | Banas et al. |
| 6,270,515 B1 | 8/2001 | Linden et al. |
| 6,270,526 B1 | 8/2001 | Cox |
| 6,277,078 B1 | 8/2001 | Porat et al. |
| 6,278,379 B1 | 8/2001 | Allen et al. |
| 6,290,728 B1 | 9/2001 | Phelps et al. |
| 6,302,892 B1 | 10/2001 | Wilk |
| 6,306,141 B1 | 10/2001 | Jervis |
| 6,328,699 B1 | 12/2001 | Eigler et al. |
| 6,344,022 B1 | 2/2002 | Jarvik |
| 6,358,277 B1 | 3/2002 | Duran |
| 6,391,036 B1 | 5/2002 | Berg et al. |
| 6,398,803 B1 | 6/2002 | Layne et al. |
| 6,406,422 B1 | 6/2002 | Landesberg |
| 6,447,539 B1 | 9/2002 | Nelson et al. |
| 6,451,051 B2 | 9/2002 | Drasler et al. |
| 6,458,153 B1 | 10/2002 | Bailey et al. |
| 6,468,303 B1 | 10/2002 | Amplatz et al. |
| 6,475,136 B1 | 11/2002 | Forsell |
| 6,478,776 B1 | 11/2002 | Rosenman et al. |
| 6,485,507 B1 | 11/2002 | Walak et al. |
| 6,488,702 B1 | 12/2002 | Besselink |
| 6,491,705 B2 | 12/2002 | Gifford, III et al. |
| 6,527,698 B1 | 3/2003 | Kung et al. |
| 6,544,208 B2 | 4/2003 | Ethier et al. |
| 6,547,814 B2 | 4/2003 | Edwin et al. |
| 6,562,066 B1 | 5/2003 | Martin |
| 6,572,652 B2 | 6/2003 | Shaknovich |
| 6,579,314 B1 | 6/2003 | Lombardi et al. |
| 6,589,198 B1 | 7/2003 | Soltanpour et al. |
| 6,616,675 B1 | 9/2003 | Evard et al. |
| 6,632,169 B2 | 10/2003 | Korakianitis et al. |
| 6,638,303 B1 | 10/2003 | Campbell |
| 6,641,610 B2 | 11/2003 | Wolf et al. |
| 6,645,220 B1 | 11/2003 | Huter et al. |
| 6,652,578 B2 | 11/2003 | Bailey et al. |
| 6,685,664 B2 | 2/2004 | Levin et al. |
| 6,712,836 B1 | 3/2004 | Berg et al. |
| 6,740,115 B2 | 5/2004 | Lombardi et al. |
| 6,758,858 B2 | 7/2004 | McCrea et al. |
| 6,764,507 B2 | 7/2004 | Shanley et al. |
| 6,770,087 B2 | 8/2004 | Layne et al. |
| 6,797,217 B2 | 9/2004 | McCrea et al. |
| 6,890,350 B1 | 5/2005 | Walak |
| 6,923,829 B2 | 8/2005 | Boyle et al. |
| 6,970,742 B2 | 11/2005 | Mann et al. |
| 7,001,409 B2 | 2/2006 | Amplatz |
| 7,004,966 B2 | 2/2006 | Edwin et al. |
| 7,025,777 B2 | 4/2006 | Moore |
| 7,060,150 B2 | 6/2006 | Banas et al. |
| 7,083,640 B2 | 8/2006 | Lombardi et al. |
| 7,115,095 B2 | 10/2006 | Eigler et al. |
| 7,118,600 B2 | 10/2006 | Dua et al. |
| 7,137,953 B2 | 11/2006 | Eigler et al. |
| 7,147,604 B1 | 12/2006 | Allen et al. |
| 7,149,587 B2 | 12/2006 | Wardle et al. |

(56) References Cited

U.S. PATENT DOCUMENTS

| | | |
|---|---|---|
| 7,169,160 B1 | 1/2007 | Middleman et al. |
| 7,169,172 B2 | 1/2007 | Levine et al. |
| 7,195,594 B2 | 3/2007 | Eigler et al. |
| 7,208,010 B2 | 4/2007 | Shanley et al. |
| 7,226,558 B2 | 6/2007 | Nieman et al. |
| 7,245,117 B1 | 7/2007 | Joy et al. |
| 7,294,115 B1 | 11/2007 | Wilk |
| 7,306,756 B2 | 12/2007 | Edwin et al. |
| 7,402,899 B1 | 7/2008 | Whiting et al. |
| 7,439,723 B2 | 10/2008 | Allen et al. |
| 7,468,071 B2 | 12/2008 | Edwin et al. |
| 7,483,743 B2 | 1/2009 | Mann et al. |
| 7,498,799 B2 | 3/2009 | Allen et al. |
| 7,509,169 B2 | 3/2009 | Eigler et al. |
| 7,550,978 B2 | 6/2009 | Joy et al. |
| 7,578,899 B2 | 8/2009 | Edwin et al. |
| 7,590,449 B2 | 9/2009 | Mann et al. |
| 7,615,010 B1 | 11/2009 | Najafi et al. |
| 7,621,879 B2 | 11/2009 | Eigler et al. |
| 7,679,355 B2 | 3/2010 | Allen et al. |
| 7,717,854 B2 | 5/2010 | Mann et al. |
| 7,794,473 B2 | 9/2010 | Tessmer et al. |
| 7,839,153 B2 | 11/2010 | Joy et al. |
| 7,842,083 B2 | 11/2010 | Shanley et al. |
| 7,854,172 B2 | 12/2010 | O'Brien et al. |
| 7,862,513 B2 | 1/2011 | Eigler et al. |
| 7,914,639 B2 | 3/2011 | Layne et al. |
| 7,939,000 B2 | 5/2011 | Edwin et al. |
| 7,988,724 B2 | 8/2011 | Salahieh et al. |
| 7,993,383 B2 | 8/2011 | Hartley et al. |
| 8,012,194 B2 | 9/2011 | Edwin et al. |
| 8,016,877 B2 | 9/2011 | Seguin et al. |
| 8,021,420 B2 | 9/2011 | Dolan |
| 8,025,625 B2 | 9/2011 | Allen |
| 8,025,668 B2 | 9/2011 | McCartney |
| 8,043,360 B2 | 10/2011 | McNamara et al. |
| 8,070,708 B2 | 12/2011 | Rottenberg et al. |
| 8,091,556 B2 | 1/2012 | Keren et al. |
| 8,096,959 B2 | 1/2012 | Stewart et al. |
| 8,137,605 B2 | 3/2012 | McCrea et al. |
| 8,142,363 B1 | 3/2012 | Eigler et al. |
| 8,147,545 B2 | 4/2012 | Avior |
| 8,157,852 B2 | 4/2012 | Bloom et al. |
| 8,157,860 B2 | 4/2012 | McNamara et al. |
| 8,157,940 B2 | 4/2012 | Edwin et al. |
| 8,158,041 B2 | 4/2012 | Colone |
| 8,187,321 B2 | 5/2012 | Shanley et al. |
| 8,202,313 B2 | 6/2012 | Shanley et al. |
| 8,206,435 B2 | 6/2012 | Shanley et al. |
| 8,216,398 B2 | 7/2012 | Bledsoe et al. |
| 8,235,916 B2 | 8/2012 | Whiting et al. |
| 8,235,933 B2 | 8/2012 | Keren et al. |
| 8,246,677 B2 | 8/2012 | Ryan |
| 8,287,589 B2 | 10/2012 | Otto et al. |
| 8,298,150 B2 | 10/2012 | Mann et al. |
| 8,298,244 B2 | 10/2012 | Garcia et al. |
| 8,303,511 B2 | 11/2012 | Eigler et al. |
| 8,313,524 B2 | 11/2012 | Edwin et al. |
| 8,328,751 B2 | 12/2012 | Keren et al. |
| 8,337,650 B2 | 12/2012 | Edwin et al. |
| 8,348,996 B2 | 1/2013 | Tuval et al. |
| 8,357,193 B2 | 1/2013 | Phan et al. |
| 8,398,708 B2 | 3/2013 | Meiri et al. |
| 8,460,366 B2 | 6/2013 | Rowe |
| 8,468,667 B2 | 6/2013 | Straubinger et al. |
| 8,480,594 B2 | 7/2013 | Eigler et al. |
| 8,579,966 B2 | 11/2013 | Seguin et al. |
| 8,597,225 B2 | 12/2013 | Kapadia |
| 8,617,337 B2 | 12/2013 | Layne et al. |
| 8,617,441 B2 | 12/2013 | Edwin et al. |
| 8,652,284 B2 | 2/2014 | Bogert et al. |
| 8,665,086 B2 | 3/2014 | Miller et al. |
| 8,696,611 B2 | 4/2014 | Nitzan et al. |
| 8,790,241 B2 | 7/2014 | Edwin et al. |
| 8,882,697 B2 | 11/2014 | Celermajer et al. |
| 8,882,798 B2 | 11/2014 | Schwab et al. |
| 8,911,489 B2 | 12/2014 | Ben-Muvhar |
| 9,005,155 B2 | 4/2015 | Sugimoto |
| 9,034,034 B2 | 5/2015 | Nitzan et al. |
| 9,055,917 B2 | 6/2015 | Mann et al. |
| 9,060,696 B2 | 6/2015 | Eigler et al. |
| 9,067,050 B2 | 6/2015 | Gallagher et al. |
| 9,205,236 B2 | 12/2015 | McNamara et al. |
| 9,220,429 B2 | 12/2015 | Nabutovsky et al. |
| 9,232,997 B2 | 1/2016 | Sugimoto et al. |
| 9,358,371 B2 | 6/2016 | McNamara et al. |
| 9,393,115 B2 | 7/2016 | Tabor et al. |
| 9,456,812 B2 | 10/2016 | Finch et al. |
| 9,622,895 B2 | 4/2017 | Cohen et al. |
| 9,629,715 B2 | 4/2017 | Nitzan et al. |
| 9,681,948 B2 | 6/2017 | Levi et al. |
| 9,707,382 B2 | 7/2017 | Nitzan et al. |
| 9,713,696 B2 | 7/2017 | Yacoby et al. |
| 9,724,499 B2 | 8/2017 | Rottenberg et al. |
| 9,757,107 B2 | 9/2017 | McNamara et al. |
| 9,789,294 B2 | 10/2017 | Taft et al. |
| 9,918,677 B2 | 3/2018 | Eigler et al. |
| 9,943,670 B2 | 4/2018 | Keren et al. |
| 9,980,815 B2 | 5/2018 | Nitzan et al. |
| 10,045,766 B2 | 8/2018 | McNamara et al. |
| 10,047,421 B2 | 8/2018 | Khan et al. |
| 10,076,403 B1 | 9/2018 | Eigler et al. |
| 10,105,103 B2 | 10/2018 | Goldshtein et al. |
| 10,111,741 B2 | 10/2018 | Michalak |
| 10,207,087 B2 | 2/2019 | Keren et al. |
| 10,207,807 B2 | 2/2019 | Moran et al. |
| 10,251,740 B2 | 4/2019 | Eigler et al. |
| 10,251,750 B2 | 4/2019 | Alexander et al. |
| 10,265,169 B2 | 4/2019 | Desrosiers et al. |
| 10,299,687 B2 | 5/2019 | Nabutovsky et al. |
| 10,357,320 B2 | 7/2019 | Beira |
| 10,357,357 B2 | 7/2019 | Levi et al. |
| 10,368,981 B2 | 8/2019 | Nitzan et al. |
| 10,463,490 B2 | 11/2019 | Rottenberg et al. |
| 10,478,594 B2 | 11/2019 | Yacoby et al. |
| 10,548,725 B2 | 2/2020 | Alkhatib et al. |
| 10,561,423 B2 | 2/2020 | Sharma |
| 10,583,002 B2 | 3/2020 | Lane et al. |
| 10,639,459 B2 | 5/2020 | Nitzan et al. |
| 10,828,151 B2 | 11/2020 | Nitzan et al. |
| 10,835,394 B2 | 11/2020 | Nae et al. |
| 10,898,698 B1 | 1/2021 | Eigler et al. |
| 10,912,645 B2 | 2/2021 | Rottenberg et al. |
| 10,925,706 B2 | 2/2021 | Eigler et al. |
| 10,940,296 B2 * | 3/2021 | Keren ............ A61M 27/002 |
| 11,109,988 B2 | 9/2021 | Rosen et al. |
| 11,135,054 B2 | 10/2021 | Nitzan et al. |
| 11,234,702 B1 | 2/2022 | Eigler et al. |
| 11,253,353 B2 | 2/2022 | Levi et al. |
| 11,255,379 B2 | 2/2022 | Baskin et al. |
| 11,291,807 B2 | 4/2022 | Eigler et al. |
| 11,304,831 B2 | 4/2022 | Nae et al. |
| 11,382,747 B2 | 7/2022 | Rottenberg et al. |
| 11,458,287 B2 | 10/2022 | Eigler et al. |
| 11,497,631 B2 | 11/2022 | Rosen et al. |
| 11,607,327 B2 | 3/2023 | Nae et al. |
| 11,612,385 B2 | 3/2023 | Nae et al. |
| 11,690,976 B2 | 7/2023 | Yacoby et al. |
| 11,813,386 B2 | 11/2023 | Nae et al. |
| 11,850,138 B2 | 12/2023 | Eigler et al. |
| 11,865,282 B2 | 1/2024 | Nae et al. |
| 2001/0007956 A1 | 7/2001 | Letac et al. |
| 2001/0021872 A1 | 9/2001 | Bailey et al. |
| 2002/0051730 A1 | 5/2002 | Bodnar et al. |
| 2002/0099431 A1 | 7/2002 | Armstrong et al. |
| 2002/0120277 A1 | 8/2002 | Hauschild et al. |
| 2002/0165479 A1 | 11/2002 | Wilk |
| 2002/0165606 A1 | 11/2002 | Wolf et al. |
| 2002/0169371 A1 | 11/2002 | Gilderdale |
| 2002/0169377 A1 | 11/2002 | Khairkhahan et al. |
| 2002/0173742 A1 | 11/2002 | Keren et al. |
| 2002/0183628 A1 | 12/2002 | Reich et al. |
| 2003/0028213 A1 | 2/2003 | Thill et al. |
| 2003/0045902 A1 | 3/2003 | Weadock |

(56) References Cited

U.S. PATENT DOCUMENTS

| | | |
|---|---|---|
| 2003/0100920 A1 | 5/2003 | Akin et al. |
| 2003/0125798 A1 | 7/2003 | Martin |
| 2003/0136417 A1 | 7/2003 | Fonseca et al. |
| 2003/0139819 A1 | 7/2003 | Beer et al. |
| 2003/0176914 A1 | 9/2003 | Rabkin et al. |
| 2003/0209835 A1 | 11/2003 | Chun et al. |
| 2003/0216679 A1 | 11/2003 | Wolf et al. |
| 2003/0216803 A1 | 11/2003 | Ledergerber |
| 2004/0010219 A1 | 1/2004 | McCusker et al. |
| 2004/0016514 A1 | 1/2004 | Nien |
| 2004/0073242 A1 | 4/2004 | Chanduszko |
| 2004/0077988 A1 | 4/2004 | Tweden et al. |
| 2004/0088045 A1 | 5/2004 | Cox |
| 2004/0093075 A1 | 5/2004 | Kuehne |
| 2004/0102797 A1 | 5/2004 | Golden et al. |
| 2004/0116999 A1 | 6/2004 | Ledergerber |
| 2004/0138743 A1 | 7/2004 | Myers et al. |
| 2004/0147869 A1 | 7/2004 | Wolf et al. |
| 2004/0147871 A1 | 7/2004 | Burnett |
| 2004/0147886 A1 | 7/2004 | Bonni |
| 2004/0147969 A1 | 7/2004 | Mann et al. |
| 2004/0162514 A1 | 8/2004 | Alferness et al. |
| 2004/0193261 A1 | 9/2004 | Berreklouw |
| 2004/0210190 A1 | 10/2004 | Kohler et al. |
| 2004/0210307 A1 | 10/2004 | Khairkhahan |
| 2004/0225352 A1 | 11/2004 | Osborne et al. |
| 2005/0003327 A1 | 1/2005 | Elian et al. |
| 2005/0033327 A1 | 2/2005 | Gainor et al. |
| 2005/0033351 A1 | 2/2005 | Newton |
| 2005/0065589 A1 | 3/2005 | Schneider et al. |
| 2005/0125032 A1 | 6/2005 | Whisenant et al. |
| 2005/0137682 A1 | 6/2005 | Justino |
| 2005/0148925 A1 | 7/2005 | Rottenberg et al. |
| 2005/0165344 A1 | 7/2005 | Dobak, III |
| 2005/0182486 A1 | 8/2005 | Gabbay |
| 2005/0267524 A1 | 12/2005 | Chanduszko |
| 2005/0283231 A1 | 12/2005 | Haug et al. |
| 2005/0288596 A1 | 12/2005 | Eigler et al. |
| 2005/0288706 A1 | 12/2005 | Widomski et al. |
| 2005/0288786 A1 | 12/2005 | Chanduszko |
| 2006/0009800 A1 | 1/2006 | Christianson et al. |
| 2006/0025857 A1 | 2/2006 | Bergheim et al. |
| 2006/0052821 A1 | 3/2006 | Abbott et al. |
| 2006/0111660 A1 | 5/2006 | Wolf et al. |
| 2006/0111704 A1 | 5/2006 | Brenneman et al. |
| 2006/0116710 A1 | 6/2006 | Corcoran et al. |
| 2006/0122522 A1 | 6/2006 | Chavan et al. |
| 2006/0122647 A1 | 6/2006 | Callaghan et al. |
| 2006/0167541 A1 | 7/2006 | Lattouf |
| 2006/0184231 A1 | 8/2006 | Rucker |
| 2006/0212110 A1 | 9/2006 | Osborne et al. |
| 2006/0241745 A1 | 10/2006 | Solem |
| 2006/0256611 A1 | 11/2006 | Bednorz et al. |
| 2006/0282157 A1 | 12/2006 | Hill et al. |
| 2007/0010852 A1 | 1/2007 | Blaeser et al. |
| 2007/0021739 A1 | 1/2007 | Weber |
| 2007/0043435 A1 | 2/2007 | Seguin et al. |
| 2007/0073337 A1 | 3/2007 | Abbott et al. |
| 2007/0129756 A1 | 6/2007 | Abbott et al. |
| 2007/0191863 A1 | 8/2007 | De Juan, Jr. et al. |
| 2007/0213813 A1 | 9/2007 | Von Segesser et al. |
| 2007/0249985 A1 | 10/2007 | Brenneman et al. |
| 2007/0276413 A1 | 11/2007 | Nobles |
| 2007/0276414 A1 | 11/2007 | Nobles |
| 2007/0282157 A1 | 12/2007 | Rottenberg et al. |
| 2007/0299384 A1 | 12/2007 | Faul et al. |
| 2008/0034836 A1 | 2/2008 | Eigler et al. |
| 2008/0086205 A1 | 4/2008 | Gordy et al. |
| 2008/0125861 A1 | 5/2008 | Webler et al. |
| 2008/0171944 A1 | 7/2008 | Brenneman et al. |
| 2008/0177300 A1 | 7/2008 | Mas et al. |
| 2008/0243081 A1 | 10/2008 | Nance et al. |
| 2008/0262602 A1 | 10/2008 | Wilk et al. |
| 2008/0264102 A1 | 10/2008 | Berra |
| 2008/0319525 A1 | 12/2008 | Tieu et al. |
| 2009/0030499 A1 | 1/2009 | Bebb et al. |
| 2009/0054976 A1 | 2/2009 | Tuval et al. |
| 2009/0125104 A1 | 5/2009 | Hoffman |
| 2009/0149947 A1 | 6/2009 | Frohwitter |
| 2009/0198315 A1 | 8/2009 | Boudjemline |
| 2009/0276040 A1 | 11/2009 | Rowe et al. |
| 2009/0319037 A1 | 12/2009 | Rowe et al. |
| 2010/0004740 A1 | 1/2010 | Seguin et al. |
| 2010/0022940 A1 | 1/2010 | Thompson |
| 2010/0057192 A1 | 3/2010 | Celermajer |
| 2010/0069836 A1 | 3/2010 | Satake |
| 2010/0070022 A1 | 3/2010 | Kuehling |
| 2010/0081867 A1 | 4/2010 | Fishler et al. |
| 2010/0100167 A1 | 4/2010 | Bortlein et al. |
| 2010/0121434 A1 | 5/2010 | Paul et al. |
| 2010/0179590 A1 | 7/2010 | Fortson et al. |
| 2010/0191326 A1 | 7/2010 | Alkhatib |
| 2010/0249491 A1 | 9/2010 | Farnan et al. |
| 2010/0249909 A1 | 9/2010 | McNamara et al. |
| 2010/0249910 A1 | 9/2010 | McNamara et al. |
| 2010/0249915 A1 | 9/2010 | Zhang |
| 2010/0256548 A1 | 10/2010 | McNamara et al. |
| 2010/0256753 A1 | 10/2010 | McNamara et al. |
| 2010/0298755 A1 | 11/2010 | McNamara et al. |
| 2010/0324652 A1 | 12/2010 | Aurilia et al. |
| 2011/0022057 A1 | 1/2011 | Eigler et al. |
| 2011/0022157 A1 | 1/2011 | Essinger et al. |
| 2011/0054515 A1 | 3/2011 | Bridgeman et al. |
| 2011/0071623 A1 | 3/2011 | Finch et al. |
| 2011/0071624 A1 | 3/2011 | Finch et al. |
| 2011/0093059 A1 | 4/2011 | Fischell et al. |
| 2011/0106149 A1 | 5/2011 | Ryan et al. |
| 2011/0152923 A1 | 6/2011 | Fox |
| 2011/0190874 A1 | 8/2011 | Celermajer et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg et al. |
| 2011/0251675 A1 | 10/2011 | Dwork |
| 2011/0257723 A1 | 10/2011 | McNamara |
| 2011/0264191 A1 | 10/2011 | Rothstein |
| 2011/0264203 A1 | 10/2011 | Dwork et al. |
| 2011/0276086 A1 | 11/2011 | Al-Qbandi et al. |
| 2011/0295182 A1 | 12/2011 | Finch et al. |
| 2011/0295183 A1 | 12/2011 | Finch et al. |
| 2011/0295362 A1 | 12/2011 | Finch et al. |
| 2011/0295366 A1 | 12/2011 | Finch et al. |
| 2011/0306916 A1 | 12/2011 | Nitzan et al. |
| 2011/0319806 A1 | 12/2011 | Wardle |
| 2012/0022507 A1 | 1/2012 | Najafi et al. |
| 2012/0022633 A1 | 1/2012 | Olson et al. |
| 2012/0035590 A1 | 2/2012 | Whiting et al. |
| 2012/0041422 A1 | 2/2012 | Whiting et al. |
| 2012/0046528 A1 | 2/2012 | Eigler et al. |
| 2012/0046739 A1 | 2/2012 | Von Oepen et al. |
| 2012/0053686 A1 | 3/2012 | McNamara et al. |
| 2012/0071918 A1 | 3/2012 | Amin et al. |
| 2012/0130301 A1 | 5/2012 | McNamara et al. |
| 2012/0165928 A1 | 6/2012 | Nitzan et al. |
| 2012/0179172 A1 | 7/2012 | Paul, Jr. et al. |
| 2012/0190991 A1 | 7/2012 | Bornzin et al. |
| 2012/0265296 A1 | 10/2012 | McNamara et al. |
| 2012/0271277 A1 | 10/2012 | Fischell et al. |
| 2012/0271398 A1 | 10/2012 | Essinger et al. |
| 2012/0289882 A1 | 11/2012 | McNamara et al. |
| 2012/0290062 A1 | 11/2012 | McNamara et al. |
| 2013/0030521 A1 | 1/2013 | Nitzan et al. |
| 2013/0046373 A1 | 2/2013 | Cartledge et al. |
| 2013/0096965 A1 | 4/2013 | Pappas et al. |
| 2013/0138145 A1 | 5/2013 | Von Oepen |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0197423 A1 | 8/2013 | Keren et al. |
| 2013/0197547 A1 | 8/2013 | Fukuoka et al. |
| 2013/0197629 A1 | 8/2013 | Gainor et al. |
| 2013/0204175 A1 | 8/2013 | Sugimoto |
| 2013/0231737 A1 | 9/2013 | McNamara et al. |
| 2013/0261531 A1 | 10/2013 | Gallagher et al. |

(56) References Cited

U.S. PATENT DOCUMENTS

| | | |
|---|---|---|
| 2013/0281988 A1 | 10/2013 | Magnin et al. |
| 2013/0304192 A1 | 11/2013 | Chanduszko |
| 2013/0331864 A1 | 12/2013 | Jelich et al. |
| 2014/0012181 A1 | 1/2014 | Sugimoto et al. |
| 2014/0012303 A1 | 1/2014 | Heipl |
| 2014/0012368 A1 | 1/2014 | Sugimoto et al. |
| 2014/0012369 A1 | 1/2014 | Murry, III et al. |
| 2014/0039599 A1 | 2/2014 | Berreklouw |
| 2014/0067037 A1 | 3/2014 | Fargahi |
| 2014/0094904 A1 | 4/2014 | Salahieh et al. |
| 2014/0128795 A1 | 5/2014 | Keren et al. |
| 2014/0128796 A1 | 5/2014 | Keren et al. |
| 2014/0163449 A1 | 6/2014 | Rottenberg et al. |
| 2014/0194971 A1 | 7/2014 | McNamara |
| 2014/0213959 A1 | 7/2014 | Nitzan et al. |
| 2014/0222144 A1 | 8/2014 | Eberhardt et al. |
| 2014/0249621 A1 | 9/2014 | Eidenschink |
| 2014/0257167 A1 | 9/2014 | Celermajer |
| 2014/0275916 A1 | 9/2014 | Nabutovsky et al. |
| 2014/0277045 A1 | 9/2014 | Fazio et al. |
| 2014/0277054 A1 | 9/2014 | McNamara et al. |
| 2014/0303710 A1 | 10/2014 | Zhang et al. |
| 2014/0350565 A1 | 11/2014 | Yacoby et al. |
| 2014/0350658 A1 | 11/2014 | Benary et al. |
| 2014/0350661 A1 | 11/2014 | Schaeffer |
| 2014/0350669 A1 | 11/2014 | Gillespie et al. |
| 2014/0357946 A1 | 12/2014 | Golden et al. |
| 2014/0364941 A1 | 12/2014 | Edmiston et al. |
| 2015/0005810 A1 | 1/2015 | Center et al. |
| 2015/0034217 A1 | 2/2015 | Vad |
| 2015/0039084 A1 | 2/2015 | Levi et al. |
| 2015/0066140 A1 | 3/2015 | Quadri et al. |
| 2015/0073539 A1 | 3/2015 | Geiger et al. |
| 2015/0112383 A1 | 4/2015 | Sherman et al. |
| 2015/0119796 A1 | 4/2015 | Finch |
| 2015/0127093 A1 | 5/2015 | Hosmer et al. |
| 2015/0142049 A1 | 5/2015 | Delgado et al. |
| 2015/0148731 A1 | 5/2015 | McNamara et al. |
| 2015/0148896 A1 | 5/2015 | Karapetian et al. |
| 2015/0157455 A1 | 6/2015 | Hoang et al. |
| 2015/0173897 A1 | 6/2015 | Raanani et al. |
| 2015/0182334 A1 | 7/2015 | Bourang et al. |
| 2015/0190229 A1 | 7/2015 | Seguin |
| 2015/0196383 A1 | 7/2015 | Johnson |
| 2015/0201998 A1 | 7/2015 | Roy et al. |
| 2015/0209143 A1 | 7/2015 | Duffy et al. |
| 2015/0230924 A1 | 8/2015 | Miller et al. |
| 2015/0238314 A1 | 8/2015 | Bortlein et al. |
| 2015/0245908 A1 | 9/2015 | Nitzan et al. |
| 2015/0272731 A1 | 10/2015 | Racchini et al. |
| 2015/0282790 A1 | 10/2015 | Quinn et al. |
| 2015/0282931 A1 | 10/2015 | Brunnett et al. |
| 2015/0294313 A1 | 10/2015 | Kamal et al. |
| 2015/0313599 A1 | 11/2015 | Johnson et al. |
| 2015/0335801 A1 | 11/2015 | Farnan et al. |
| 2015/0359556 A1 | 12/2015 | Vardi |
| 2016/0007924 A1 | 1/2016 | Eigler et al. |
| 2016/0022423 A1 | 1/2016 | McNamara et al. |
| 2016/0022970 A1 | 1/2016 | Forcucci et al. |
| 2016/0045165 A1 | 2/2016 | Braido et al. |
| 2016/0045311 A1 | 2/2016 | McCann et al. |
| 2016/0073907 A1 | 3/2016 | Nabutovsky et al. |
| 2016/0120550 A1 | 5/2016 | McNamara et al. |
| 2016/0129260 A1 | 5/2016 | Mann et al. |
| 2016/0157862 A1 | 6/2016 | Hernandez et al. |
| 2016/0166381 A1 | 6/2016 | Sugimoto et al. |
| 2016/0184561 A9 | 6/2016 | McNamara et al. |
| 2016/0206423 A1 | 7/2016 | O'Connor et al. |
| 2016/0213467 A1 | 7/2016 | Backus et al. |
| 2016/0220360 A1 | 8/2016 | Lin et al. |
| 2016/0220365 A1 | 8/2016 | Backus et al. |
| 2016/0262878 A1 | 9/2016 | Backus et al. |
| 2016/0262879 A1 | 9/2016 | Meiri et al. |
| 2016/0287386 A1 | 10/2016 | Alon et al. |
| 2016/0296325 A1 | 10/2016 | Edelman et al. |
| 2016/0361167 A1 | 12/2016 | Tuval et al. |
| 2016/0361184 A1 | 12/2016 | Tabor et al. |
| 2017/0035435 A1 | 2/2017 | Amin et al. |
| 2017/0056171 A1 | 3/2017 | Cooper et al. |
| 2017/0112624 A1 | 4/2017 | Patel |
| 2017/0113026 A1 | 4/2017 | Finch |
| 2017/0128705 A1 | 5/2017 | Forcucci et al. |
| 2017/0135685 A9 | 5/2017 | McNamara et al. |
| 2017/0165062 A1 | 6/2017 | Rothstein |
| 2017/0165532 A1 | 6/2017 | Khan et al. |
| 2017/0216025 A1 | 8/2017 | Nitzan et al. |
| 2017/0224323 A1 | 8/2017 | Rowe et al. |
| 2017/0224444 A1 | 8/2017 | Viecilli et al. |
| 2017/0231766 A1 | 8/2017 | Hariton et al. |
| 2017/0273790 A1 | 9/2017 | Vettukattil et al. |
| 2017/0281339 A1 | 10/2017 | Levi et al. |
| 2017/0312486 A1 | 11/2017 | Nitzan et al. |
| 2017/0319823 A1 | 11/2017 | Yacoby et al. |
| 2017/0325956 A1 | 11/2017 | Rottenberg et al. |
| 2017/0340460 A1 | 11/2017 | Rosen et al. |
| 2017/0348100 A1 | 12/2017 | Lane et al. |
| 2018/0028314 A1 | 2/2018 | Ekvall et al. |
| 2018/0099128 A9 | 4/2018 | McNamara et al. |
| 2018/0104053 A1 | 4/2018 | Alkhatib et al. |
| 2018/0110609 A1 | 4/2018 | Ehnes et al. |
| 2018/0125630 A1 | 5/2018 | Hynes et al. |
| 2018/0130988 A1 | 5/2018 | Nishikawa et al. |
| 2018/0200496 A1 | 7/2018 | Kratzberg et al. |
| 2018/0243071 A1* | 8/2018 | Eigler .................. A61F 2/2487 |
| 2018/0256865 A1 | 9/2018 | Finch et al. |
| 2018/0263766 A1 | 9/2018 | Nitzan et al. |
| 2018/0280667 A1 | 10/2018 | Keren |
| 2018/0280668 A1 | 10/2018 | Alaswad |
| 2018/0344994 A1 | 12/2018 | Karavany et al. |
| 2019/0000327 A1 | 1/2019 | Doan et al. |
| 2019/0008628 A1 | 1/2019 | Eigler et al. |
| 2019/0015103 A1 | 1/2019 | Sharma |
| 2019/0015188 A1 | 1/2019 | Eigler et al. |
| 2019/0021861 A1 | 1/2019 | Finch |
| 2019/0083076 A1 | 3/2019 | Alanbaei |
| 2019/0110911 A1 | 4/2019 | Nae et al. |
| 2019/0239754 A1 | 8/2019 | Nabutovsky et al. |
| 2019/0254814 A1 | 8/2019 | Nitzan et al. |
| 2019/0262118 A1 | 8/2019 | Eigler et al. |
| 2019/0328513 A1 | 10/2019 | Levi et al. |
| 2019/0336163 A1 | 11/2019 | McNamara et al. |
| 2020/0060825 A1 | 2/2020 | Rottenberg et al. |
| 2020/0078196 A1 | 3/2020 | Rosen et al. |
| 2020/0078558 A1 | 3/2020 | Yacoby et al. |
| 2020/0085600 A1 | 3/2020 | Schwartz et al. |
| 2020/0197178 A1 | 6/2020 | Vecchio |
| 2020/0261705 A1 | 8/2020 | Nitzan et al. |
| 2020/0315599 A1 | 10/2020 | Nae et al. |
| 2020/0368505 A1 | 11/2020 | Nae et al. |
| 2021/0022507 A1 | 1/2021 | Williams |
| 2021/0052378 A1 | 2/2021 | Nitzan et al. |
| 2021/0100665 A1 | 4/2021 | Nae et al. |
| 2021/0121179 A1 | 4/2021 | Ben-David et al. |
| 2021/0205590 A1 | 7/2021 | Fahey et al. |
| 2022/0008014 A1 | 1/2022 | Rowe et al. |
| 2022/0211361 A1 | 7/2022 | Rolando et al. |
| 2022/0304803 A1 | 9/2022 | Guyenot et al. |

FOREIGN PATENT DOCUMENTS

| | | |
|---|---|---|
| CN | 101505680 A | 8/2009 |
| CN | 105555204 A | 5/2016 |
| CN | 108451569 A | 8/2018 |
| EP | 1987777 A2 | 11/2008 |
| EP | 2238933 A1 | 10/2010 |
| EP | 2305321 A1 | 4/2011 |
| EP | 1965842 B1 | 11/2011 |
| EP | 3400907 A1 | 11/2018 |
| FR | 2827153 A1 | 1/2003 |
| WO | WO-9531945 A1 | 11/1995 |
| WO | WO-9702850 A1 | 1/1997 |
| WO | WO-9727898 A1 | 8/1997 |
| WO | WO-9960941 A1 | 12/1999 |
| WO | WO-0044311 A2 | 8/2000 |

(56) References Cited

FOREIGN PATENT DOCUMENTS

| | | |
|---|---|---|
| WO | WO-0050100 A1 | 8/2000 |
| WO | WO-0110314 A2 | 2/2001 |
| WO | WO-0126585 A1 | 4/2001 |
| WO | WO-0191828 A2 | 12/2001 |
| WO | WO-0226281 A1 | 4/2002 |
| WO | WO-02071974 A2 | 9/2002 |
| WO | WO-02087473 A1 | 11/2002 |
| WO | WO-03053495 A2 | 7/2003 |
| WO | WO-2005027752 A1 | 3/2005 |
| WO | WO-2005074367 A2 | 8/2005 |
| WO | WO-2006127765 A1 | 11/2006 |
| WO | WO-2007083288 A2 | 7/2007 |
| WO | WO-2008055301 A1 | 5/2008 |
| WO | WO-2008070797 A2 | 6/2008 |
| WO | WO-2009029261 A1 | 3/2009 |
| WO | WO-2010128501 A1 | 11/2010 |
| WO | WO-2010129089 A2 | 11/2010 |
| WO | WO-2010139771 A2 | 12/2010 |
| WO | WO-2010139771 A3 | 1/2011 |
| WO | WO-2011062858 A1 | 5/2011 |
| WO | WO-2013096965 A1 | 6/2013 |
| WO | WO-2013172474 A1 | 11/2013 |
| WO | WO-2016178171 A1 | 11/2016 |
| WO | WO-2017118920 A1 | 7/2017 |
| WO | WO-2018158747 A1 | 9/2018 |
| WO | WO-2019015617 A1 | 1/2019 |
| WO | WO-2019085841 A1 | 5/2019 |
| WO | WO-2019109013 A1 | 6/2019 |
| WO | WO-2019142152 A1 | 7/2019 |
| WO | WO-2019179447 A1 | 9/2019 |
| WO | WO-2019212812 A1 | 11/2019 |
| WO | WO-2019218072 A1 | 11/2019 |
| WO | WO-2020206062 A1 | 10/2020 |
| WO | WO-2020257530 A1 | 12/2020 |
| WO | WO-2021050589 A1 | 3/2021 |
| WO | WO-2021113670 A1 | 6/2021 |
| WO | WO-2021212011 A2 | 10/2021 |
| WO | WO-2021224736 A1 | 11/2021 |
| WO | WO-2022046921 A1 | 3/2022 |
| WO | WO-2022076601 A1 | 4/2022 |
| WO | WO-2022091018 A1 | 5/2022 |
| WO | WO-2022091019 A1 | 5/2022 |
| WO | WO-2022103973 A1 | 5/2022 |

OTHER PUBLICATIONS

Abraham et al., "Sustained efficacy of pulmonary artery pressure to guide adjustment of chronic heart failure therapy: complete follow-up results from the CHAMPION randomised trial," The Lancet, http://dx.doi.org/10.1016/S0140-6736(15)00723-0 (2015).

Abraham et al., "Wireless pulmonary artery haemodynamic monitoring in chronic heart failure: a randomised controlled trial," The Lancet, DOI:10.1016/S0140-6736(11)60101-3 (2011).

Abreu et al., "Doppler ultrasonography of the femoropopliteal segment in patients with venous ulcer," J Vasc Bras., 11(4):277-285 (2012).

Adamson et al., "Ongoing Right Ventricular Hemodynamics in Heart Failure Clinical Value of Measurements Derived From an Implantable Monitoring System," J Am Coll Cardiol., 41(4):565-571 (2003).

Adamson et al., "Wireless Pulmonary Artery Pressure Monitoring Guides Management to Reduce Decompensation in Heart Failure With Preserved Ejection Fraction," Circ Heart Fail., 7:935-944 (2014).

Ambrosy et al. "The Global Health and Economic Burden of Hospitalizations for Heart Failure," J Am Coll Cardiol., 63:1123-1133 (2014).

Aminde et al., "Current diagnostic and treatment strategies for Lutembacher syndrome: the pivotal role of echocardiography," Cardiovasc Diagn Ther., 5(2):122-132 (2015).

Anderas E. "Advanced MEMS Pressure Sensors Operating in Fluids," Digital Comprehensive Summaries of Uppsala Dissertation from the Faculty of Science and Technology 933. Uppsala ISBN 978-91-554-8369-2 (2012).

Anderas et al., "Tilted c-axis Thin-Film Bulk Wave Resonant Pressure Sensors with Improved Sensitivity," IEEE Sensors J., 12(8):2653-2654 (2012).

Ando, et al., Left ventricular decompression through a patent foramen ovale in a patient with hypertrophic cardiomyopathy: A case report, Cardiovascular Ultrasound, 2: 1-7 (2004).

Article 34 Amendments dated May 28, 2013 in Int'l PCT Patent Appl. Serial No. PCT/IB2012/001859 (0810).

Article 34 Amendments dated Nov. 27, 2012 in Int'l PCT Patent Appl. Serial No. PCT/IL2011/000958 (0710).

Ataya et al., "A Review of Targeted Pulmonary Arterial Hypertension-Specific Pharmacotherapy," J. Clin. Med., 5(12):114(2016).

"Atrium Advanta V12, Balloon Expandable Covered Stent, Improving Patient Outcomes with An Endovascular Approach, " Brochure, 8 pages, Getinge (2017).

Bannan et al., "Characteristics of Adult Patients with Atrial Septal Defects Presenting with Paradoxical Embolism.," Catheterization and Cardiovascular Interventions, 74:1066-1069 (2009).

Baumgartner et al., "ESC Guidelines for the management of grown-up congenital heart disease (new version 2010)—The Task Force on the Management of Grown-up Congenital Heart Disease of the European Society of Cardiology (ESC)," Eur Heart J., 31:2915-2957 (2010).

Beemath et al., "Pulmonary Embolism as a Cause of Death in Adults Who Died With Heart Failure," Am J Cardiol., 98:1073-1075 (2006).

Benza et al., "Monitoring Pulmonary Arterial Hypertension Using an Implantable Hemodynamic Sensor," CHEST, 156(6):1176-1186 (2019).

Boehm, et al., "Balloon Atrial Septostomy: History and Technique," Images Paeditr. Cardiol., 8(1):8-14 (2006).

Braunwald, Heart Disease, Chapter 6, pp. 186.

Bridges, et al., "The Society of Thoracic Surgeons Practice Guideline Series: Transmyocardial Laser Revascularization," Ann Thorac Surg., 77:1494-1502 (2004).

Bristow, et al., "Improvement in cardiac myocyte function by biological effects of medical therapy: a new concept in the treatment of heart failure," European Heart Journal, 16 (Suppl.F):20-31 (1995).

Bruch et al., "Fenestrated Occluders for Treatment of ASD in Elderly Patients with Pulmonary Hypertension and/or Right Heart Failure," J Interven Cardiol., 21(1):44-49 (2008).

Burkhoff et al., "Assessment of systolic and diastolic ventricular properties via pressure-volume analysis: a guide for clinical, translational, and basic researchers," Am J Physiol Heart Circ Physiol., 289:H501-H512 (2005).

Butler et al. "Recognizing Worsening Chronic Heart Failure as an Entity and an End Point in Clinical Trials," JAMA., 312(8):789-790 (2014).

Case, et al., "Relief of High Left-Atrial Pressure in Left-Ventricular Failure," Lancet, (pp. 841-842), Oct. 17, 1964.

Chakko et al., "Clinical, radiographic, and hemodynamic correlations in chronic congestive heart failure: conflicting results may lead to inappropriate care," Am J Medicine, 90:353-359 (1991) (Abstract Only).

Chang et al., "State-of-the-art and recent developments in micro/nanoscale pressure sensors for smart wearable devices and health monitoring systems," Nanotechnology and Precision Engineering, 3:43-52 (2020).

Chen et al., "Continuous wireless pressure monitoring and mapping with ultra-small passive sensors for health monitoring and critical care," Nature Communications, 5(1):1-10 (2014).

Chen et al., "National and Regional Trends in Heart Failure Hospitalization and Mortality Rates for Medicare Beneficiaries, 1998-2008," JAMA, 306(15):1669-1678 (2011).

Chiche et al., "Prevalence of patent foramen ovale and stroke in pulmonary embolism patients," Eur Heart J., 34:P1142 (2013) (Abstract Only).

Chin et al., "The right ventricle in pulmonary hypertension," Coron Artery Dis., 16(1):13-18 (2005) (Abstract Only).

(56) References Cited

OTHER PUBLICATIONS

Chun et al., "Lifetime Analysis of Hospitalizations and Survival of Patients Newly Admitted With Heart Failure," Circ Heart Fail., 5:414-421 (2012).
Ciarka et al., "Atrial Septostomy Decreases Sympathetic Overactivity in Pulmonary Arterial Hypertension," Chest, 131(6):P1831-1837 (2007) (Abstract Only).
Cleland et al., "The EuroHeart Failure survey programme—a survey on the quality of care among patients with heart failure in Europe—Part 1: patient characteristics and diagnosis," Eur Heart J., 24:442-463 (2003).
Clowes et al., "Mechanisms of Arterial Graft Healing—Rapid Transmural Capillary Ingrowth Provides a Source of Intimal Endothelium and Smooth Muscle in Porous PTFE Prostheses," Am J Pathol., 123:220-230 (1986).
Coats, et al., "Controlled Trial of Physical Training in Chronic Heart Failure: Exercise Performance, Hemodynamics, Ventilation, and Autonomic Function," Circulation, 85: 2119-2131 (1992).
Davies et al., "Abnormal left heart function after operation for atrial septal defect," British Heart Journal, 32:747-753 (1970).
Davies, et al., "Reduced Contraction and Altered Frequency Response of Isolated Ventricular Myocytes From Patients With Heart Failure, Circulation," 92: 2540-2549 (1995).
Del Trigo et al., "Unidirectional Left-To-Right Interatrial Shunting for Treatment of Patients with Heart Failure with Reduced Ejection Fraction: a Safety and Proof-of-Principle Cohort Study," Lancet, 387:1290-1297 (2016).
Della Lucia et al., "Design, fabrication and characterization of SAW pressure sensors for offshore oil and gas exploration," Sensors and Actuators A: Physical, 222:322-328 (2015).
Drazner et al., "Prognostic Importance of Elevated Jugular Venous Pressure and a Third Heart Sound in Patients with Heart Failure," N Engl J Med., 345(8):574-81 (2001).
Drazner et al., "Relationship between Right and Left-Sided Filling Pressures in 1000 Patients with Advanced Heart Failure," Heart Lung Transplant, 18:1126-1132 (1999).
Drexel, et al., "The Effects of Cold Work and Heat Treatment on the Properties of Nitinol Wire, Proceedings of the International Conference on Shape Memory and Superelastic Technologies, SMST 2006," Pacific Grove, California, USA (pp. 447-454) May 7-11, 2006.
Eigler et al., "Cardiac Unloading with an Implantable Interatrial Shunt in Heart Failure: Serial Observations in an Ovine Model of Ischemic Cardiomyopathy," Structural Heart, 1:40-48 (2017).
Eigler, et al., Implantation and Recovery of Temporary Metallic Stents in Canine Coronary Arteries, JACC, 22(4):1207-1213 (1993).
Ennezat, et al., An unusual case of low-flow, low gradient severe aortic stenosis: Left-to-right shunt due to atrial septal defect, Cardiology, 113(2):146-148, (2009).
Eshaghian et al., "Relation of Loop Diuretic Dose to Mortality in Advanced Heart Failure," Am J Cardiol., 97:1759-1764 (2006).
Ewert, et al., Acute Left Heart Failure After Interventional Occlusion of An Artial Septal Defect, Z Kardiol, 90(5): 362-366 (May 2001).
Ewert, et al., Masked Left Ventricular Restriction in Elderly Patients With Atrial Septal Defects: A Contraindication for Closure?, Catheterization and Cardiovascular Intervention, 52:177-180 (2001).
Extended European Search Report dated Jan. 8, 2015 in EP Patent Appl No. 10772089.8. (0530).
Extended European Search Report dated Mar. 29, 2019 in EP Patent Appl. Serial No. EP16789391 (1830).
Extended European Search Report dated Sep. 19, 2006 in EP Patent Appl No. 16170281.6 (0731).
Feldman et al., "Transcatheter Interatrial Shunt Device for the Treatment of Heart Failure with Preserved Ejection Fraction (Reduce LAP-HF I [Reduce Elevated Left Atrial Pressure in Patients With Heart Failure]), A Phase 2, Randomized, Sham-Controlled Trial," Circulation, 137:364-375 (2018).
Ferrari et al., "Impact of pulmonary arterial hypertension (PAH) on the lives of patients and carers: results from an international survey," Eur Respir J., 42:26312 (2013) (Abstract Only).
Fonarow et al., "Characteristics, Treatments, and Outcomes of Patients With Preserved Systolic Function Hospitalized for Heart Failure," J Am Coll Cardiol., 50(8):768-777 (2007).
Fonarow et al., "Risk Stratification for In-Hospital Mortality in Acutely Decompensated Heart Failure: Classification and Regression Tree Analysis," JAMA, 293(5):572-580 (2005).
Fonarow, G., "The Treatment Targets in Acute Decompensated Heart Failure," Rev Cardiovasc Med., 2:(2):S7-S12 (2001).
Galie et al., "2015 ESC/ERS Guidelines for the diagnosis and treatment of pulmonary hypertension—The Joint Task Force for the Diagnosis and Treatment of Pulmonary Hypertension of the European Society of Cardiology (ESC) and the European Respiratory Society (ERS)," European Heart Journal, 37:67-119 (2016).
Galie et al., "Pulmonary arterial hypertension: from the kingdom of the near-dead to multiple clinical trial meta-analyses," Eur Heart J., 31:2080-2086 (2010).
Galipeau et al., "Surface acoustic wave microsensors and applications," Smart Materials and Structures, 6(6):658-667 (1997) (Abstract Only).
Geiran, et al., Changes in cardiac dynamics by opening an interventricular shunt in dogs, J. Surg. Res. 48(1):6-12 (1990).
Gelernter-Yaniv, et al., Transcatheter ClosureoOf Left-To-Right Interatrial Shunts to Resolve Hypoxemia, Congenit. Heart Dis. 31(1): 47-53 (Jan. 2008).
Geva et al., "Atrial septal defects," Lancet, 383:1921-32 (2014).
Gewillig, et al., Creation with a stent of an unrestrictive lasting atrial communication, Cardio. Young 12(4): 404-407 (2002).
Gheorghiade et al., "Acute Heart Failure Syndromes, Current State and Framework for Future Research," Circulation, 112:3958-3968 (2005).
Gheorghiade et al., "Effects of Tolvaptan, a Vasopressin Antagonist, in Patients Hospitalized With Worsening Heart Failure A Randomized Controlled Trial," JAMA., 291:1963-1971 (2004).
Go et al. "Heart Disease and Stroke Statistics—2014 Update—A Report From the American Heart Association," Circulation, 128:1-267 (2014).
Guillevin et al., "Understanding the impact of pulmonary arterial hypertension on patients' and carers' lives," Eur Respir Rev., 22:535-542 (2013).
Guyton et al., "Effect of Elevated Left Atrial Pressure and Decreased Plasma Protein Concentration on the Development of Pulmonary Edema," Circulation Research, 7:643-657 (1959).
Hasenfub, et al., A Transcatheter Intracardiac Shunt Device for Heart Failure with Preserved Ejection Fraction (Reduce LAP-HF): A Multicentre, Open-Label, Single-Arm, Phase 1 Trial, www.thelancet.com, 387:1298-1304 (2016).
Hoeper et al., "Definitions and Diagnosis of Pulmonary Hypertension," J Am Coll Cardiol., 62(5):D42-D50 (2013).
Hogg et al., "Heart Failure With Preserved Left Ventricular Systolic Function. Epidemiology, Clinical Characteristics, and Prognosis," J Am Coll Cardiol., 43(3):317-327 (2004).
Howell et al., "Congestive heart failure and outpatient risk of venous thromboembolism: A retrospective, case-control study," Journal of Clinical Epidemiology, 54:810-816 (2001).
Huang et al., "Remodeling of the chronic severely failing ischemic sheep heart after coronary microembolization: functional, energetic, structural, and cellular responses," Am J Physiol Heart Circ Physiol., 286:H2141-H2150 (2004).
Humbert et al., "Pulmonary Arterial Hypertension in France—Results from a National Registry," Am J Respir Crit Care Med., 173:1023-1030 (2006).
International Search Report & Written Opinion dated Nov. 7, 2016 in Int'l PCT Patent Appl. Serial No. PCT/IB2016/052561 (1810).
International Search Report & Written Opinion dated May 29, 2018 in Int'l PCT Patent Appl. Serial No. PCT/IB2018/051385 (1310).
International Search Report & Written Opinion dated Feb. 6, 2013 in Int'l PCT Patent Appl. No. PCT/IB2012/001859, 12 pages (0810).
International Search Report & Written Opinion dated Feb. 7, 2020 in Int'l PCT Patent Appl. Serial No. PCT/IB2019/060257 (1410).

(56) References Cited

OTHER PUBLICATIONS

International Search Report & Written Opinion dated May 13, 2019 in Int'l PCT Patent Appl. No. PCT/IB2019/050452 (1610).
International Search Report & Written Opinion dated May 29, 2018 in Int'l PCT Patent Appl. Serial No. PCTIB2018/051355 (1310).
International Search Report & Written Opinion dated Jul. 14, 2020 in Int'l PCT Patent Appl. Serial No. PCT/IB2020/053832 (1210).
International Search Report & Written Opinion dated Jul. 20, 2020 in Int'l PCT Patent Appl. Serial No. PCT/IB2020/054699 (1710 PCT).
International Search Report & Written Opinion dated Aug. 12, 2020 in Int'l PCT Patent Appl. Serial No. PCT/IB2020/053118 (1010).
International Search Report & Written Opinion dated Aug. 28, 2012 in Int'l PCT Patent Appl. No. PCT/IL2011/000958 (0710).
International Search Report & Written Opinion dated Sep. 21, 2020 in Int'l PCT Patent Appl. Serial No. PCT/IB2020/054306 (1510).
International Search Report & Written Opinion dated Oct. 11, 2017 in Int'l PCT Patent Appl. Serial No. PCT/IB2017/053188 (1110).
International Search Report & Written Opinion dated Oct. 26, 2007 in Int'l PCT Patent Appl. Serial No. PCT/IB07/50234 (0610).
International Search Report dated Apr. 7, 2008 in Int'l PCT Patent Appl. Serial No. PCT/IL05/00131 (0410).
International Search Report dated Aug. 25, 2010 in Intl PCT Patent Appl. Serial No. PCT/IL2010/000354 (0510).
ISR & Written Opinion dated Feb. 16, 2015 in Int'l PCT Patent Appl. Serial No. PCT/IB2014/001771 (0910).
Jessup et al. "2009Focused Update: ACC/AHA Guidelines for the Diagnosisand Management of Heart Failure in Adults: A Report of the American College ofCardiology Foundation/American Heart Association Task Force on PracticeGuidelines: Developed in Collaboration With the International Society for Heartand Lung Transplantation," J. Am. Coll. Cardiol., 53:1343-1382 (2009).
Jiang, G., "Design challenges of implantable pressure monitoring system," Frontiers in Neuroscience, 4(29):1-4 (2010).
Kane et al., "Integration of clinical and hemodynamic parameters in the prediction of long-term survival in patients with pulmonary arterial hypertension," Chest, 139(6):1285-1293 (2011) (Abstract Only).
Kaye et al., "Effects of an Interatrial Shunt on Rest and Exercise Hemodynamics: Results of a Computer Simulation in Heart Failure," Journal of Cardiac Failure, 20(3): 212-221 (2014).
Kaye et al., "One-Year Outcomes After Transcatheter Insertion of an Interatrial Shunt Device for the Management of Heart Failure With Preserved Ejection Fraction," Circulation: Heart Failure, 9(12):e003662 (2016).
Keogh et al., "Interventional and Surgical Modalitiesof Treatment in Pulmonary Hypertension," J Am Coll Cardiol., 54:S67-77 (2009).
Khositseth et al., Transcatheter Amplatzer Device Closure of Atrial Septal Defect and Patent Foramen Ovale in Patients With Presumed Paradoxical Embolism, Mayo Clinic Proc., 79:35-41 (2004).
Kramer, et al., Controlled Trial of Captopril in Chronic Heart Failure: A Rest and Exercise Hemodynamic Study, Circulation, 67(4): 807-816, 1983.
Kretschmar et al., "Shunt Reduction With a Fenestrated Amplatzer Device," Catheterization and Cardiovascular Interventions, 76:564-571 (2010).
Kropelnicki et al., "CMOS-compatible ruggedized high-temperature Lamb wave pressure sensor," J. Micromech. Microeng., 23:085018 pp. 1-9 (2013).
Krumholz et al., "Patterns of Hospital Performance in Acute Myocardial Infarction and Heart Failure 30-Day Mortality and Readmission," Circ Cardiovasc Qual Outcomes, 2:407-413 (2009).
Kulkarni et al., "Lutembacher's syndrome," J Cardiovasc Did Res., 3(2):179-181 (2012).
Kurzyna et al., "Atrial Septostomy in Treatment of End-Stage Right Heart Failure in Patients With Pulmonary Hypertension," Chest, 131:977-983 (2007).
Lai et al., Bidirectional Shunt Through a Residual Atrial Septal Defect After Percutaneous Transvenous Mitral Commissurotomy, Cadiology, 83(3): 205-207 (1993).
Lammers et al., "Efficacy and Long-Term Patency of Fenerstrated Amplatzer Devices in Children," Catheter Cardiovasc Interv., 70:578-584 (2007).
Lemmer, et al., Surgical Implications of Atrial Septal Defect Complicating Aortic Balloon Valvuloplasty, Ann. thorac. Surg, 48(2):295-297 (Aug. 1989).
Lindenfeld et al. "Executive Summary: HFSA 2010 Comprehensive Heart Failure Practice Guideline," J. Cardiac Failure, 16(6):475-539 (2010).
Luo, Yi, *Selective and Regulated RF Heating of Stent Toward Endohyperthermia Treatment of In-Stent Restenosis*, A Thesis Submitted in Partial Fulfillment of The Requirements For The Degree of Master of Applied Science in The Faculty of Graduate and Postdoctoral Studies (Electrical and Computer Engineering), The University of British Columbia, Vancouver, Dec. 2014.
MacDonald et al., "Emboli Enter Penetrating Arteries of Monkey Brain in Relation to Their Size," Stroke, 26:1247-1251 (1995).
Maluli et al., "Atrial Septostomy: A Contemporary Review," Clin. Cardiol., 38(6):395-400 (2015).
Maurer et al., "Rationale and Design of the Left Atrial Pressure Monitoring to Optimize Heart Failure Therapy Study (LAPTOP-HF)," Journal of Cardiac Failure., 21(6): 479-488 (2015).
McClean et al., "Noninvasive Calibration of Cardiac Pressure Transducers in Patients With Heart Failure: An Aid to Implantable Hemodynamic Monitoring and Therapeutic Guidance," J Cardiac Failure, 12(7):568-576 (2006).
McLaughlin et al., "Management of Pulmonary Arterial Hypertension," J Am Coll Cardiol., 65(18):1976-1997 (2015).
McLaughlin et al., "Survival in Primary Pulmonary Hypertension—The Impact of Epoprostenol Therapy.," Circulation, 106:1477-1482 (2002).
Merriam-Webster OnLine Dictionary, Definition of "chamber", printed Dec. 20, 2004.
Mu et al., "Dual mode acoustic wave sensor for precise pressure reading," Applied Physics Letters, 105:113507-1-113507-5 (2014).
Nagaragu et al., "A 400μW Differential FBAR Sensor Interface IC with digital readout," IEEE., pp. 218-221 (2015).
Noordegraaf et al., "The role of the right ventricle in pulmonary arterial hypertension," Eur Respir Rev., 20(122):243-253 (2011).
O'Byrne et al., "The effect of atrial septostomy on the concentration of brain-type natriuretic peptide in patients with idiopathic pulmonary arterial hypertension," Cardiology in the Young, 17(5):557-559 (2007) (Abstract Only).
Oktay et al., "The Emerging Epidemic of Heart Failure with Preserved Ejection Fraction," Curr Heart Fail Rep., 10(4):1-17 (2013).
Owan et al., "Trends in Prevalence and Outcome of Heart Failure with Preserved Ejection Fraction," N Engl J Med., 355:251-259 (2006).
Paitazoglou et al., "Title: The Afr-Prelieve Trial: A prospective, non-randomized, pilot study to assess the Atrial Flow Regulator (AFR) in Heart Failure Patients with either preserved or reduced ejection fraction," EuroIntervention, 28:2539-50 (2019).
Park Blade Septostomy Catheter Instructions for Use, Cook Medical, 28 pages, Oct. 2015.
Park, et al., Blade Atrial Septostomy: Collaborative Study, Circulation, 66(2):258-266 (1982).
Partial Supplemental European Search Report dated Dec. 11, 2018 in EP Patent Appl. Serial No. 16789391.6 (1830).
Peters et al., "Self-fabricated fenestrated Amplatzer occluders for transcatheter closure of atrial septal defect in patients with left ventricular restriction: midterm results," Clin Res Cardiol., 95:88-92 (2006).
Ponikowski et al., "2016 ESC Guidelines for the diagnosis and treatment of acute and chronic heart failure. The Task Force for the diagnosis and treatment of acute and chronic heart failure of the European Society of Cardiology (ESC)," Eur Heart J., doi:10.1093/eurheartj/ehw128 (2016).
Potkay, J. A., "Long term, implantable blood pressure monitoring systems," Biomed Microdevices, 10:379-392 (2008).
Pretorious et al., "An Implantable Left Atrial Pressure Sensor Lead Designed for Percutaneous Extraction Using Standard Techniques," PACE, 00:1-8 (2013).

(56) References Cited

OTHER PUBLICATIONS

Rajeshkumar et al., "Atrial septostomy with a predefined diameter using a novel occlutech atrial flow regulator improves symptoms and cardiac index in patients with severe pulmonary arterial hypertension," Catheter Cardiovasc Interv., 1-9 (2017).
Rich et al., "Atrial Septostomy as Palliative Therapy for Refractory Primary Pulmonary Hypertension," Am J Cardiol., 51:1560-1561 (1983).
Ritzema et al., "Direct Left Atrial Pressure Monitoring in Ambulatory Heart Failure Patients—Initial Experience With a New Permanent Implantable Device," Circulation, 116:2952-2959 (2007).
Ritzema et al., "Physician-Directed Patient Self-Management of Left Atrial Pressure in Advanced Chronic Heart Failure," Circulation, 121:1086-1095 (2010).
Roberts et al., "Integrated microscopy techniques for comprehensive pathology evaluation of an implantable left atrial pressure sensor," J Histotechnology, 36(1):17-24 (2013).
Rodes-Cabau et al., "Interatrial Shunting for Heart Failure Early and Late Results From the First-in-Human Experience With the V-Wave System," J Am Coll Cardiol Intv., 11:2300-2310.doi:10.1016/j.cin. 2018.07.001 (2018).
Rosenquist et al., Atrial Septal Thickness and Area in Normal Heart Specimens and in Those With Ostium Secundum Atrial Septal Defects, J. Clin. Ultrasound, 7:345-348 (1979).
Ross et al., "Interatrial Communication and Left Atrial Hypertension—A Cause of Continuous Murmur," Circulation, 28:853-860 (1963).
Rossignol, et al., Left-to-Right Atrial Shunting: New Hope for Heart Failure, www.thelancet.com, 387:1253-1255 (2016).
Roven, Effect of Compromising Right Ventricular Function in Left Ventricular Failure by Means of Interatrial and Other Shunts 24:209-219 (Aug. 1969).
Salehian, et al., Improvements in Cardiac Form and Function After Transcatheter Closure of Secundum Atrial Septal Defects, Journal of the American College of Cardiology, 45(4):499-504 (2005).
Sandoval et al., "Effect of atrial septostomy on the survival of patients with severe pulmonary arterial hypertension," Eur Respir J., 38:1343-1348 (2011).
Sandoval et al., "Graded Balloon Dilation Atrial Septostomy in Severe Primary Pulmonary Hypertension—A Therapeutic Alternative for Patients Nonresponsive to Vasodilator Treatment," JACC, 32(2):297-304 (1998).
Schiff et al., "Decompensated heart failure: symptoms, patterns of onset, and contributing factors," Am J. Med., 114(8):625-630 (2003) (Abstract Only).
Schmitto, et al., Chronic Heart Failure Induced by Multiple Sequential Coronary Microembolization in sheep, The International Journal of Artificial Organs, 31(4):348-353 (2008).
Schneider et al., "Fate of a Modified Fenestration of Atrial Septal Occluder Device after Transcatheter Closure of Atrial Septal Defects in Elderly Patients," J Interven Cardiol., 24:485-490 (2011).
Scholl et al., "Surface Acoustic Wave Devices for Sensor Applications," Phys Status Solidi Appl Res., 185(1):47-58 (2001) (Abstract Only).
Schubert, et al., Left ventricular Conditioning in the Elderly Patient to Prevent Congestive Heart Failure After Transcatheter Closure of the Atrial Septal Defect, Catheterization and Cardiovascular Interventions, 64(3): 333-337 (2005).
Setoguchi et al., "Repeated hospitalizations predict mortality in the community population with heart failure," Am Heart J., 154:260-266 (2007).
Shah et al., "Heart Failure With Preserved, Borderline, and Reduced Ejection Fraction—5-Year Outcomes," J Am Coll Cardiol., https://doi.org/10.1016/j.jacc.2017.08.074 (2017).
Shah et al., "One-Year Safety and Clinical Outcomes of a Transcatheter Interatrial Shunt Device for the Treatment of Heart Failure With Preserved Ejection Fraction in the Reduce Elevated Left Atrial Pressure in Patients With Heart Failure (Reduce LAP-HF I) Trial—A Randomized Clinical Trial," JAMA Cardiol. doi:10.1001/jamacardio. 2018.2936 (2018).
Sitbon et al., "Selexipag for the Treatment of Pulmonary Arterial Hypertension.," N Engl J Med., 373(26):2522-2533 (2015).
Sitbon et al., "Epoprostenol and pulmonary arterial hypertension: 20 years of clinical experience," Eur Respir Rev., 26:160055:1-14 (2017).
Steimle et al., "Sustained Hemodynamic Efficacy of Therapy Tailored to Reduce Filling Pressures in Survivors With Advanced Heart Failure," Circulation, 96:1165-1172 (1997).
Stevenson et al., "The Limited Reliability of Physical Signs for Estimating Hemodynamics in Chronic Heart Failure," JAMA, 261(6):884-888 (1989) (Abstract Only).
Stormer, et al., Comparative Study of in Vitro Flow Characteristics Between a Human Aortic Valve and a Designed Aortic Valve and Six Corresponding Types of Prosthetic Heart Valves, European Surgical Research 8(2):117-131 (1976).
Stumper, et al., Modified Technique of Stent Fenestration of the Atrial Septum, Heart, 89:1227-1230, (2003).
Su et al., "A film bulk acoustic resonator pressure sensor based on lateral field excitation," International Journal of DistributedSensor Networks, 14(11):1-8 (2018).
Supplementary European Search Report dated Nov. 13, 2009 in EP Patent Appl. Serial No. 05703174.2 (0430).
Thenappan et al., "Evolving Epidemiology of Pulmonary Arterial Hypertension," Am J Resp Critical Care Med., 186:707-709 (2012).
Tomai et al., "Acute Left Ventricular Failure After Transcatheter Closure of a Secundum Atrial Septal Defect in a Patient With Coronary Artery Disease: A Critical Reappraisal," Catheterization and Cardiovascular Interventions, 55:97-99 (2002).
Torbicki et al., "Atrial Septostomy," The Right Heart, 305-316 (2014).
Trainor, et al., Comparative Pathology of an Implantable Left Atrial Pressure Sensor, ASAIO Journal, Clinical Cardiovascular/Cardiopulmonary Bypass, 59(5):486-492 (2013).
Troost et al., "A Modified Technique of Stent Fenestration of the Interatrial Septum Improves Patients With Pulmonary Hypertension," Catheterization and Cardiovascular Interventions, 73:173179 (2009).
Troughton et al., "Direct Left Atrial Pressure Monitoring in Severe Heart Failure: Long-Term Sensor Performance," J. of Cardiovasc. Trans. Res., 4:3-13 (2011).
Vank-Noordegraaf et al., "Right Heart Adaptation to Pulmonary Arterial Hypertension—Physiology and Pathobiology," J Am Coll Cardiol., 62(25):D22-33 (2013).
Verel et al., "Comparison of left atrial pressure and wedge pulmonary capillary pressure—Pressure gradients between left atrium and left ventricle," British Heart J., 32:99-102 (1970).
Viaene et al., "Pulmonary oedema after percutaneous ASD-closure," Acta Cardiol., 65(2):257-260 (2010).
Wang et al., "A Low Temperature Drifting Acoustic Wave Pressure Sensor with an Integrated Vacuum Cavity for Absolute Pressure Sensing," Sensors, 20(1788):1-13 (2020).
Warnes et al., "ACC/AHA 2008 Guidelines for the Management of Adults With Congenital Heart Disease—A Report of the American College of Cardiology/American Heart Association Task Force on Practice Guidelines (Writing Committee to Develop Guidelines on the Management of Adults With Congenital Heart Disease)," JACC, 52(23):e143-e263 (2008).
Webb et al., "Atrial Septal Defects in the Adult Recent Progress and Overview," Circulation, 114:1645-1653 (2006).
Wiedemann, H.R., "Earliest description by Johann Friedrich Meckel, Senior (1750) of what is known today as Lutembacher syndrome (1916)," Am J Med Genet., 53(1):59-64 (1994) (Abstract Only).
Written Opinion of the International Searching Authority dated Apr. 7, 2008 in Int'l PCT Patent Appl. Serial No. PCT/IL05/00131 (0410).
Yantchev et al., "Thin Film Lamb Wave Resonators in Frequency Control and Sensing Applications: A Review," Journal of Micromechanics and Microengineering, 23(4):043001 (2013).
Zhang et al., "Acute left ventricular failure after transcatheter closure of a secundum atrial septal defect in a patient with hypertrophic cardiomyopathy," Chin Med J., 124(4):618-621 (2011).

(56) References Cited

OTHER PUBLICATIONS

Zhang et al., "Film bulk acoustic resonator-based high-performance pressure sensor integrated with temperature control system," J Micromech Microeng., 27(4):1-10 (2017).
Zhou, et al., Unidirectional Valve Patch for Repair of Cardiac Septal Defects with Pulmonary Hypertension, Annals of Thoracic Surgeons, 60:1245-1249, (1995).
U.S. Appl. No. 09/839,643 / now U.S. Pat. No. 8,091,556, filed Apr. 20, 2001 / Jan. 10, 2012.
U.S. Appl. No. 10/597,666 / now U.S. Pat. No. 8,070,708, filed Jun. 20, 2007 / Dec. 6, 2011.
U.S. Appl. No. 12/223,080 / now U.S. Pat. No. 9,681,948, filed Jul. 16, 2014 / Jun. 20, 2017.
U.S. Appl. No. 13/107,832 / now U.S. Pat. No. 8,235,933, filed May 13, 2011 / Aug. 7, 2012.
U.S. Appl. No. 13/107,843 / now U.S. Pat. No. 8,328,751, filed May 13, 2011 / Dec. 11, 2012.
U.S. Appl. No. 13/108,672 / now U.S. Pat. No. 9,724,499, filed May 16, 2011 / Aug. 8, 2017.
U.S. Appl. No. 13/108,698, filed Jun. 16, 2011.
U.S. Appl. No. 13/108,850, filed May 16, 2011.
U.S. Appl. No. 13/108,880 / now U.S. Pat. No. 8,696,611, filed May 16, 2011 / Apr. 15, 2014.
U.S. Appl. No. 13/193,309 / now U.S. Pat. No. 9,629,715, filed Jul. 28, 2011 / Apr. 25, 2017.
U.S. Appl. No. 13/193,335 / now U.S. Pat. No. 9,034,034, filed Jul. 28, 2011 / May 19, 2015.
U.S. Appl. No. 13/708,794 / now U.S. Pat. No. 9,943,670, filed Dec. 7, 2012 / Apr. 17, 2018.
U.S. Appl. No. 14/154,080 / now U.S. Pat. No. 10,207,807, filed Jan. 13, 2014 / Feb. 19, 2019.
U.S. Appl. No. 14/154,088, filed Jan. 13, 2014.
U.S. Appl. No. 14/154,093, filed Jan. 13, 2014.
U.S. Appl. No. 14/227,982 / now U.S. Pat. No. 9,707,382, filed Mar. 27, 2014 / Jul. 18, 2017.
U.S. Appl. No. 14/282,615 / now U.S. Pat. No. 9,713,696, filed May 20, 2014 / Jul. 25, 2017.
U.S. Appl. No. 14/712,801 / now U.S. Pat. No. 9,980,815, filed May 14, 2015 / May 29, 2018.
U.S. Appl. No. 15/449,834 / now U.S. Pat. No. 10,076,403, filed Mar. 3, 2017 / Sep. 18, 2018.
U.S. Appl. No. 15/492,852 / U.S. Pat. No. 10,368,981, filed Apr. 20, 2017 / Aug. 6, 2019.
U.S. Appl. No. 15/570,752 / now U.S. Pat. No. 10,940,296, filed Oct. 31, 2017 / Mar. 9, 2021.
U.S. Appl. No. 15/608,948, filed May 30, 2017.
U.S. Appl. No. 15/624,314 / now U.S. Pat. No. 10,357,357, filed Jun. 15, 2017 / Jul. 23, 2019.
U.S. Appl. No. 15/650,783 / now U.S. Pat. No. 10,639,459, filed Jul. 14, 2017 / May 5, 2020.
U.S. Appl. No. 15/656,936 / now U.S. Pat. No. 10,478,594, filed Jul. 21, 2017 / Nov. 19, 2019.
U.S. Appl. No. 15/668,622 / now U.S. Pat. No. 10,463,490, filed Aug. 3, 2017 / Nov. 5, 2019.
U.S. Appl. No. 15/798,250, filed Oct. 30, 2017.
U.S. Appl. No. 15/988,888 / now U.S. Pat. No. 10,828,151, filed May 24, 2018 / Nov. 10, 2020.
U.S. Appl. No. 16/130,978 / now U.S. Pat. No. 10,251,740, filed Sep. 13, 2018 / Apr. 9, 2019.
U.S. Appl. No. 16/130,988 / now U.S. Pat. No. 10,925,706, filed Sep. 13, 2018 / Feb. 23, 2021.
U.S. Appl. No. 16/205,213 / now U.S. Pat. No. 10,835,394, filed Nov. 29, 2018 / Nov. 17, 2020.
U.S. Appl. No. 16/374,698, filed Apr. 3, 2019.
U.S. Appl. No. 16/395,209, filed Apr. 25, 2019.
U.S. Appl. No. 16/408,419, filed May 9, 2019.
U.S. Appl. No. 16/505,624, filed Jul. 8, 2019.
U.S. Appl. No. 16/672,420, filed Nov. 1, 2019.
U.S. Appl. No. 16/686,013, filed Nov. 15, 2019.
U.S. Appl. No. 16/866,377, filed May 4, 2020.
U.S. Appl. No. 16/875,652 / now U.S. Pat. No. 10,898,698, filed May 15, 2020 Jan. 26, 2021.
U.S. Appl. No. 16/876,640, filed May 18, 2020.
U.S. Appl. No. 16/878,228 / now U.S. Pat. No. 10,912,645, filed May 19, 2020 Feb. 9, 2021.
U.S. Appl. No. 16/963,139, filed Jul. 17, 2020.
U.S. Appl. No. 17/092,063, filed Nov. 6, 2020.
U.S. Appl. No. 17/092,081, filed Nov. 6, 2020.
U.S. Appl. No. 17/095,615, filed Nov. 11, 2020.
U.S. Appl. No. 17/098,251, filed Nov. 13, 2020.
U.S. Appl. No. 17/166,771, filed Feb. 3, 2021.
U.S. Appl. No. 17/175,549, filed Feb. 12, 2021.
Borlaug, et al., Latent Pulmonary Vascular Disease May Alter The Response to Therapeutic Atrial Shunt Device in Heart Failure, Circulation (Mar. 2022).
Clowes, et al., Mechanisms of Arterial Graft Healing—Rapid Transmural Capillary Ingrowth Provides a Source of Intimal Endothelium and Smooth Muscle in Porous PTFE Prostheses, Am. J. Pathol., 123(2):220-230 (May 1986).
Flachskampf, et al., Influence of Orifice Geometry and Flow Rate on Effective Valve Area: An In Vitro Study, Journal of the American College of Cardiology, 15(5):1173-1180 (Apr. 1990).
Greitz, et al., Pulsatile Brain Movement and Associated Hydrodynamics Studied by Magnetic Resonance Phase Imaging, Diagnostic Neuroradiology, 34(5): 370-380 (1992).
International Search Report & Written Opinion dated Feb. 3, 2023 in Int'l PCT Patent Appl. Serial No. PCT/IB2022/060621 (221001).
International Search Report & Written Opinion dated Feb. 9, 2022 in Int'l PCT Patent Appl. Serial No. PCT/IB2021/060473 (201001).
International Search Report & Written Opinion dated Mar. 29, 2023 in Int'l PCT Patent Appl. Serial No. PCT/IB2023/050743 (241001).
International Search Report & Written Opinion dated May 17, 2022 in Int'l PCT Patent Appl. Serial No. PCT/IB2022/051177 (231001).
International Search Report & Written Opinion dated Jul. 23, 2021 in Int'l PCT Patent Appl. Serial No. PCT/IB2021/053594 (191001).
Pfeiffer, In vivo fluid dynamics of the Ventura interatrial shunt device in patients with heart failure, ESC Heart Failure, DOI: 10.1002/ehf2.14859 (May 22, 2024).
Rodes-Cabau, et al., Interatrial shunt therapy in advanced heart failure: Outcomes from the open-label cohort of the RELIEVE-HF trial, Eur. J. Heart. Fail., 26(4):1078-1089 (Apr. 2024).
Shah, et al., Atrial Shunt Device For Heart Failure With Preserved And Mildly Reduced Ejection Fraction (Reduce LAP-HF II): A Randomised, Multicentre, Blinded, Sham-Controlled Trial, The Lancet, 399(10330):1130-1140 (Mar. 2022).
Stone, Gregg, A Double-blind, Randomized Placebo-Procedure-Controlled Trial of an Interatrial Shunt in Patients with HFrEF and HFpEF: Principal Results from the RELIEVE-HF Trial, American College of Cardiology (ACC) (Apr. 6, 2024).

\* cited by examiner

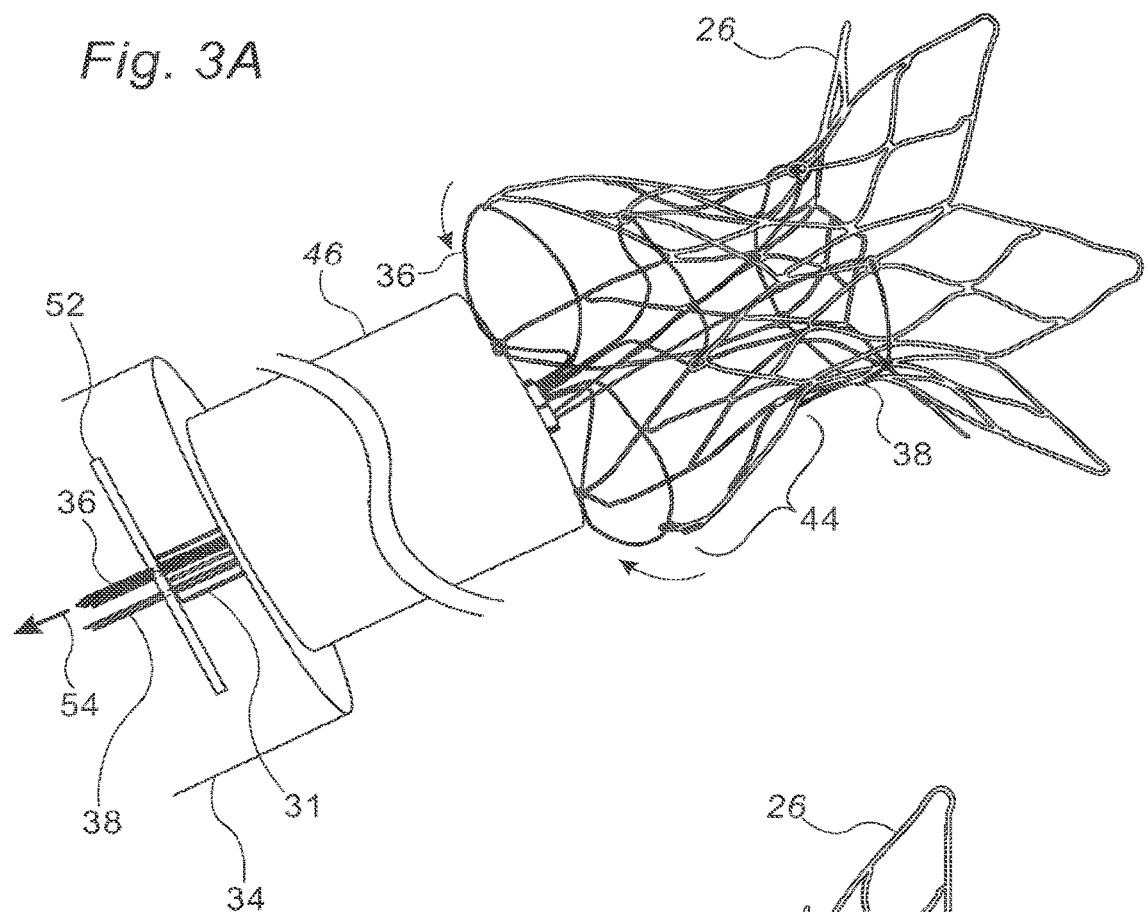
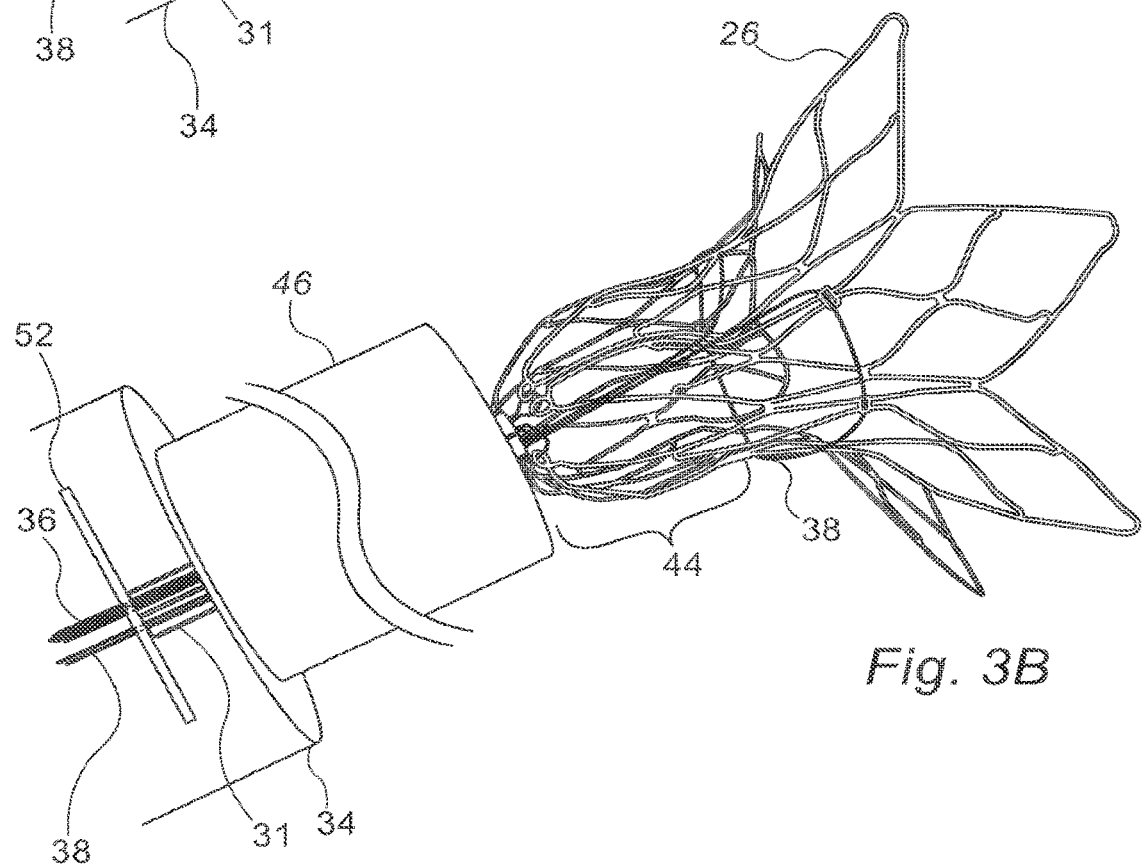

TEMPORARY INTERATRIAL SHUNTS

CROSS-REFERENCE TO RELATED APPLICATIONS

The present application is a divisional application of U.S. application Ser. No. 15/570,752, filed Oct. 31, 2017, now U.S. Pat. No. 10,940,296, which is a national phase of International PCT Patent Application No. PCT/IB2016/52561, filed May 5, 2016, which claims priority from U.S. Provisional Application 62/158,022, entitled "Percutaneous device for temporary stenting and shunting," filed May 7, 2015, the entire disclosures of each of which are incorporated herein by reference.

FIELD OF THE INVENTION

Embodiments of the present invention relate generally to the field of medical devices, and specifically to percutaneous devices for treatment of a subject.

BACKGROUND

Some medical conditions are treated by implanting a shunt between two body cavities, typically to release excess pressure from one of the cavities into the other. For example, a shunt may be implanted between the right and left atria of the heart for the treatment of pulmonary hypertension by decompression of the right atrium, or for the treatment of congestive heart failure by decompression of the left atrium. Implantable shunts of this sort are described, for example, in U.S. Pat. No. 8,091,556, whose disclosure is incorporated herein by reference.

U.S. Pat. No. 9,067,050, whose disclosure is incorporated herein by reference, describes an arteriovenous shunt assembly including a shunt and a pull wire operated flow control mechanism. The shunt has a tubular body that defines a fluid passageway between a first end and a second end thereof. The pull wire mechanism includes a portion disposed around the tubular shunt in at least one loop. The at least one loop may be selectively tightened or loosened remotely from the shunt to regulate the rate of blood flow through the tubular shunt.

US Patent Application Publication 2014/0303710, whose disclosure is incorporated herein by reference, describes a recyclable and adjustable interventional stent for intravascular constriction. The stent main body is divided into three parts and shaped like a waist drum with expansion parts being arranged on the upper and lower parts of the stent main body respectively for supporting and positioning. A variable aperture part is arranged in the middle of the stent main body. The upper expansion part is or is not provided with a coating; the middle variable aperture part and the upper half part of the lower expansion part are covered with a pericardium subjected to anti-calcification treatment; and a metal wire ring is passed through the lowermost edge of the stent. A compound conveying guide pipe is composed of an outer sheath and a core. The core is a hollow pipe and a wire hanging groove is arranged on the outer side wall of the tip of the pipe to hang the metal wire ring of the lowermost edge of the stent. A fixing bolt on the outer sheath is used for fixing the relative position between the outer sheath and the core. The stent is used to replace conventional pulmonary artery banding as, adhesion not being formed around the heart and major vessels and pulmonary stenosis not being formed, difficulties during radical surgery are not increased.

US Patent Publication 2013/0178784, whose disclosure is incorporated herein by reference, describes devices and methods for treating heart disease by normalizing elevated blood pressure in the left and right atria of a heart of a mammal. Devices may include an adjustable hydraulic diameter shunt portion which can be manually adjusted in vivo. Methods are provided for adjusting the flow rate of the devices in vivo.

U.S. Pat. No. 5,035,706, whose disclosure is incorporated herein by reference, describes a self-expanding stent formed of stainless steel wire arranged in a closed zig-zag configuration. The stent includes an endless series of straight sections joined at their ends by bends. The stent is compressible into a reduced diameter size for insertion into and removal from a body passageway. The bends of at least one end of the stent are formed into eyes for connection with the eyes at one end of a similarly constructed stent to permit single-step introduction of several lengths of stent into the passageway. A stent can include a monofilament thread passing through successive eyes at one end of the stent, the thread passing through each eye at least once and through some of the eyes a second time. The trailing ends of the thread extend from the stent and outside the body passageway. The stent can be retrieved from the body passageway by threading a tube of the free ends of the thread until the tube is adjacent the stent. The diameter at one end of the stent is reduced by pulling the free ends of the thread through the tube. A sheath concentrically disposed over the tube is introduced into the body passageway and over the remaining length of the stent to further compress the stent for removal from the passageway.

U.S. Pat. No. 6,221,096, whose disclosure is incorporated herein by reference, describes an intravascular stent having an elastic self-expandable cylindrical stent proper. The stent proper is connected to metal support wires that are long enough to reach outside of the body of a patient through a catheter. Manipulation of the support wires pushes the stent proper into a blood vessel from within the catheter, thereby allowing it to expand there, and then contracts and retracts the stent proper into the catheter, repeatedly.

U.S. Pat. No. 6,468,303, whose disclose is incorporated herein by reference, describes a collapsible medical device and associated method for shunting selected organs and vessels, wherein the medical device is shaped from a shape memory metal fabric. The device may be used, for example, to non-surgically create a transjugular intrahepatic portosystemic shunt. The device is preferably made from a continuous tubular metal fabric and includes two outer flanges that reduce device migration and includes a central passageway between the two outer flanges. The metal fabric may be heat treated within a mold in order to substantially set a desired relaxed shape of the device. The medical device includes a fastener for attaching to the end of a guide wire or delivery catheter. The medical device having the desired relaxed shape may be collapsed and delivered through a catheter or the like for deployment in a desired channel or opening in a patient's body and is retrievable after deployment.

SUMMARY OF THE INVENTION

An implanted interatrial shunt may cause various complications, such as distortion of the interatrial septum, cardiac arrhythmias, inability to use the transseptal approach for future interventions, paradoxical embolism, and/or blood desaturation. Hence, for cases in which an interatrial shunt is required only temporarily (i.e., for a short period of time, such as less than one week), an implanted shunt may not necessarily be the most appropriate solution for treatment.

Embodiments of the present invention therefore provide—as an alternative to an implanted shunt—shunting apparatus that may be placed within the subject for only a short period of time, e.g., for less than one week, or even less than one day (e.g., 2-3 hours, 3-6 hours, or 6-12 hours). The apparatus comprises a shunt, along with one or more wires that extend from the proximal portion of the shunt to the exterior of the subject. These wires, which are typically controlled via a control handle, may be used to collapse the shunt, whenever the shunt is no longer needed. Following the collapse of the shunt, the shunt may be easily withdrawn from the subject.

In some embodiments, another wire, which passes circumferentially along the intermediate portion of the shunt and also extends to the exterior of the subject, may be used to adjust the diameter of the shunt while the shunt is inside the subject, thus regulating the flow of blood across the interatrial septum.

Other temporary shunts described herein include a shunt that is coupled to a distal end of a sheath. The shunt is advanced, in a collapsed state, over a guidewire, until the shunt spans the interatrial septum. Subsequently, the guidewire is retracted while the sheath is held in place, such that a stopper coupled to the distal portion of the guidewire applies a longitudinally compressive force to the shunt, thus causing the shunt to open. The sheath is then locked with respect to the guidewire, such that the shunt remains open. Upon the conclusion of treatment, the sheath is unlocked, such that the shunt collapses, and subsequently, the shunt is removed from the subject.

(In general, within the context of medical applications, the term "shunt" may refer to (i) a passage that diverts a bodily fluid from one portion of the body to another, or (ii) a device that is used to establish, and/or maintain, such a passage. In the context of the present application, including the claims, the term "shunt" typically refers to the latter.)

There is therefore provided, in accordance with some embodiments of the present invention, apparatus that includes a shunt. The shunt includes a flared distal portion, a flared proximal portion, and an intermediate portion, disposed between the distal portion and the proximal portion. The apparatus further includes a constricting flexible longitudinal element passing circumferentially along the intermediate portion of the shunt, configured to constrict the intermediate portion of the shunt, and one or more proximal-portion-collapsing flexible longitudinal elements configured to collapse the proximal portion of the shunt.

In some embodiments, the constricting flexible longitudinal element includes a wire.

In some embodiments, the intermediate portion of the shunt is shaped to define a plurality of orifices, and the wire passes circumferentially along the intermediate portion by passing through the orifices.

In some embodiments, the proximal portion of the shunt is shaped to define a plurality of orifices, and the proximal-portion-collapsing flexible longitudinal elements include one or more wires, each of which passes through at least two of the orifices.

There is further provided, in accordance with some embodiments of the present invention, a method that includes placing a shunt between two chambers of a heart of a subject, such that one or more shunt-collapsing flexible longitudinal elements extend from a proximal portion of the shunt to an exterior of the subject. The method further includes, subsequently, using the shunt-collapsing flexible longitudinal elements, collapsing the shunt into a catheter.

In some embodiments, the method further includes, using the catheter, removing the shunt from the subject.

In some embodiments, removing the shunt from the subject includes removing the shunt from the subject after less than one week from the placement of the shunt.

In some embodiments, the two chambers of the heart are two atria of the heart.

In some embodiments, the two chambers of the heart are two ventricles of the heart.

In some embodiments, the method further includes, while the shunt is between the two chambers of the heart, constricting the shunt, using a constricting flexible longitudinal element that extends from the shunt to the exterior of the subject.

There is further provided, in accordance with some embodiments of the present invention, a method that includes placing a shunt between two atria of a subject, and, after less than one week from the placement of the shunt, withdrawing the shunt from the subject.

There is further provided, in accordance with some embodiments of the present invention, apparatus that includes a sheath, and a shunt coupled to a distal end of the sheath, the shunt being configured to open from a collapsed state to an open state upon a longitudinally compressive force being applied to the shunt.

In some embodiments, the shunt includes a plurality of wires, distal ends of which are joined together, and proximal ends of which are coupled to the sheath.

In some embodiments, the shunt is configured to open by the wires expanding radially outward from each other.

In some embodiments, in the open state, a proximal portion of the shunt and a distal portion of the shunt are wider than an intermediate portion of the shunt that is between the proximal portion of the shunt and the distal portion of the shunt.

In some embodiments, the apparatus further includes:
a guidewire, and
a stopper coupled to a distal portion of the guidewire, the stopper being configured to apply the longitudinally compressive force to the shunt by pressing against a distal portion of the shunt when the sheath and the shunt are over the guidewire.

In some embodiments, the shunt is shaped to define a distal aperture configured to fittingly receive the stopper.

In some embodiments, the stopper includes a bead.

There is further provided, in accordance with some embodiments of the present invention, a method that includes passing a guidewire across a septum that separates between a first chamber of a heart of a subject and a second chamber of the heart, such that a stopper coupled to the guidewire is in the second chamber. The method further includes, subsequently, passing a shunt, in a collapsed state, over the guidewire, until a proximal portion of the shunt is in the first chamber, and a distal portion of the shunt is in the second chamber, and subsequently, using the stopper, opening the shunt from the collapsed state to an open state.

In some embodiments, opening the shunt includes opening the shunt by, using the stopper, pressing against the distal portion of the shunt.

In some embodiments, the shunt is shaped to define a distal aperture, and pressing against the distal portion of the shunt includes pressing against the distal portion of the shunt while the stopper is fittingly received by the distal aperture.

In some embodiments, the first chamber is a right atrium, and the second chamber is a left atrium.

In some embodiments, the first chamber is a right ventricle, and the second chamber is a left ventricle.

In some embodiments, the shunt is coupled to a distal end of a sheath, and the method further includes, subsequently to opening the shunt, maintaining the open state of the shunt by locking the sheath with respect to the guidewire.

In some embodiments, the method further includes:
causing the shunt to collapse, by unlocking the sheath with respect the guidewire; and
subsequently, removing the shunt from the subject.

In some embodiments, removing the shunt from the subject includes removing the shunt from the subject after less than one week from the opening of the shunt.

The present invention will be more fully understood from the following detailed description of embodiments thereof, taken together with the drawings, in which:

BRIEF DESCRIPTION OF THE DRAWINGS

FIG. 3A-C collectively show a technique for removing a shunt from a subject, in accordance with some embodiments of the present invention.

DETAILED DESCRIPTION OF EMBODIMENTS

Figure 1:
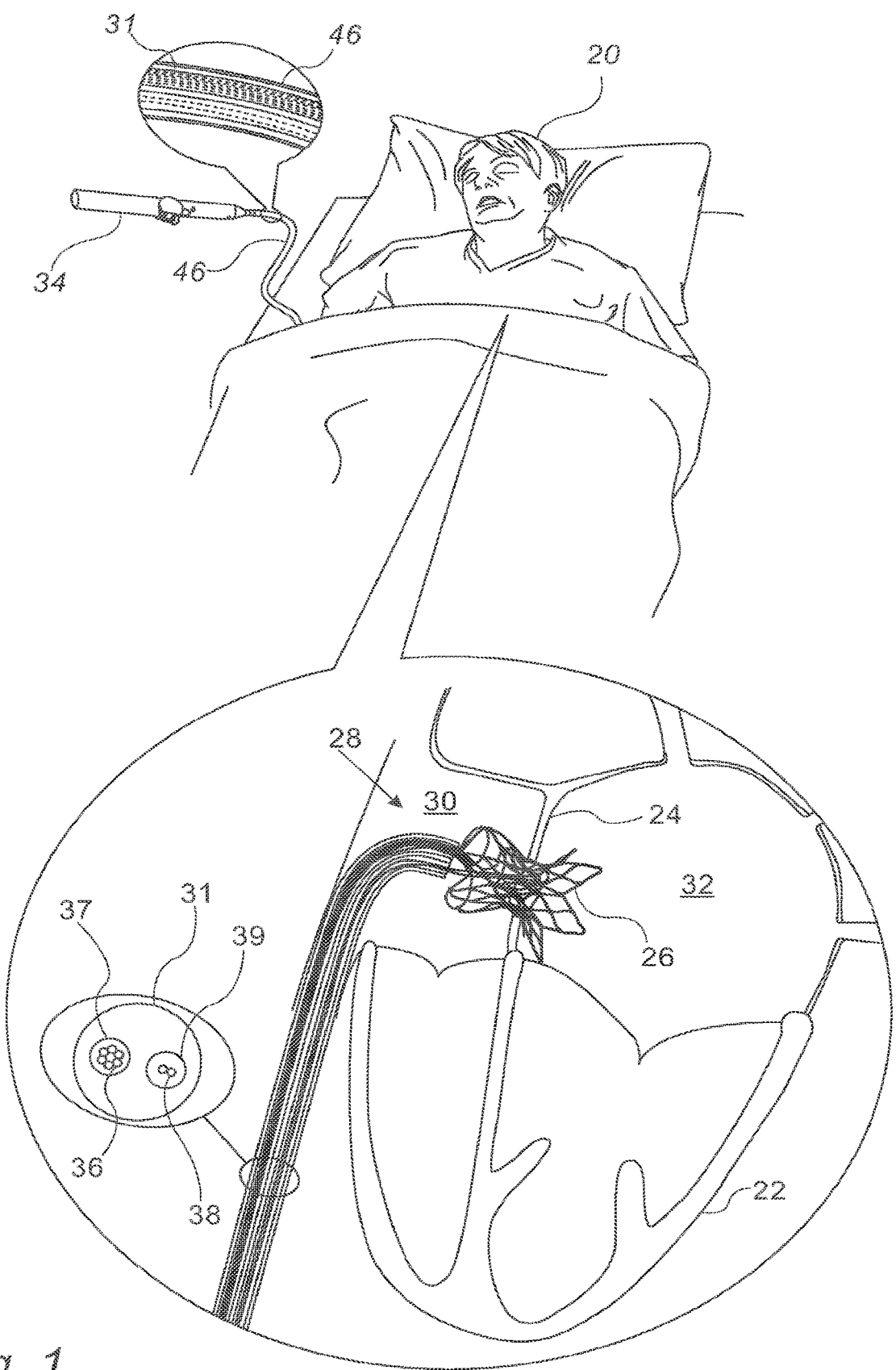
FIG. 1 is a schematic illustration of a temporary shunt apparatus inside a subject, in accordance with some embodiments of the present invention.
Figure 2:
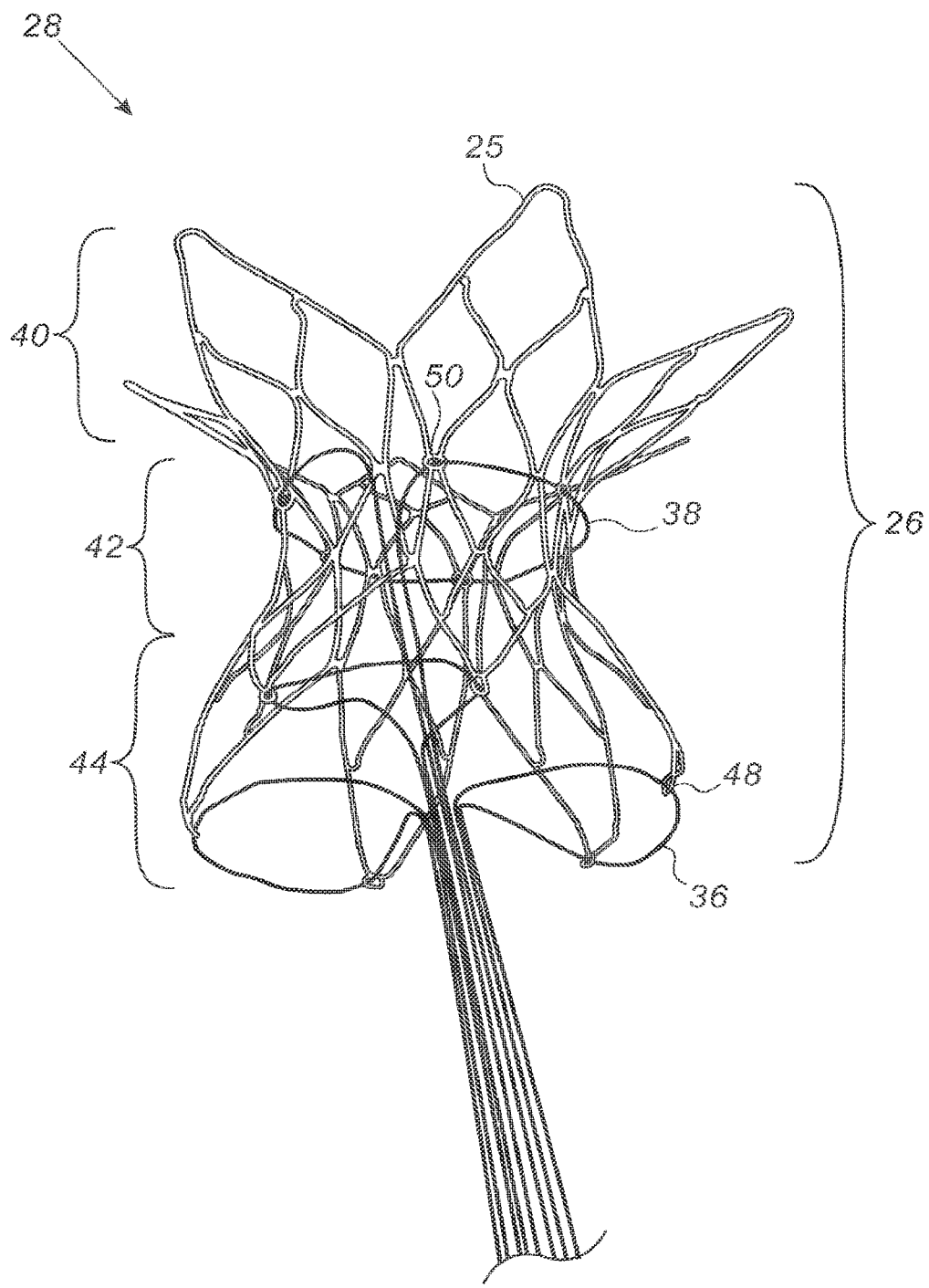
FIG. 2 is a schematic illustration of a temporary shunt apparatus, in accordance with some embodiments of the present invention.

Reference is initially made to FIG. 1, which is a schematic illustration of a temporary shunt apparatus 28 inside a subject 20, and to FIG. 2, which is a schematic illustration of temporary shunt apparatus 28, in accordance with some embodiments of the present invention.

Apparatus 28 comprises a shunt 26, which may be placed between two chambers of the heart 22 of subject 20, such as within the interatrial septum 24 of heart 22, between the right atrium 30 and the left atrium 32. Alternatively, the shunt may be placed between the two ventricles of the heart, or between any other two body cavities. Shunt 26 typically comprises a flared distal portion 40, a flared proximal portion 44, and an intermediate portion 42, which is disposed between distal portion 40 and proximal portion 44. Distal portion 40 and proximal portion 44 anchor the shunt to septum 24 (i.e., prevent migration of the shunt from within the septum), while intermediate portion 42 provides a passageway across the septum, through which blood may flow. Typically, shunt 26 comprises a shape-memory material, such as Nitinol, such that the shunt expands to its natural shape (the shape shown in FIGS. 1-2) upon being released from a delivery catheter, as further described below. (It is noted that, for clarity, shunt apparatus 28 is drawn disproportionately large, relative to heart 22, in FIG. 1.)

In the context of the present application, including the claims, the proximal and distal portions of the shunt are "flared," in that these portions extend radially outward from the intermediate portion of the stent. In some embodiments, as shown, each of the proximal and distal portions of the shunt comprises a plurality of leaves 25, such as, for example, six leaves 25, as shown. In other embodiments, the proximal portion and/or the distal portion does not comprise a plurality of leaves, but rather, is shaped to define a flared ring, or has some other suitable form.

To facilitate removal of the shunt, embodiments described herein provide one or more shunt-collapsing flexible longitudinal elements, which extend from proximal portion 44 to the exterior of the subject. For example, as shown in the figures, the shunt-collapsing flexible longitudinal elements may comprise wires 36. Typically, while inside the subject, wires 36 are contained within a lumen 37 of a sheath 31 passing between proximal portion 44 and the exterior of the subject. (For example, sheath 31 may exit the subject via a femoral vein of the subject.) As further described below with reference to FIG. 3A, as wires 36 are pulled, wires 36 exert an inward radial force on the proximal portion of the shunt, such that the proximal portion of the shunt is collapsed. Typically, as shown in FIG. 1, the proximal ends of wires 36 are coupled to control handle 34, via which wires 36 may be pulled (or alternatively, released, such as to allow the proximal portion of the shunt to expand).

Typically, wires 36 remain coupled to the shunt throughout the time that the shunt is in place inside the subject. Due to wires 36 remaining coupled to the shunt, the shunt may be easily removed immediately upon receiving indication that further shunting is no longer required. In this respect, embodiments described herein differ from other, hypothetical shunting applications in which (i) the shunt is removed only in the event of a complication, and (ii) to remove the shunt, it is necessary to use a lasso or other specialized shunt-removal instrument.

FIG. 2 shows a particular embodiment in which proximal portion 44 is shaped to define a plurality of orifices 48, and each of wires 36 passes through at least two of orifices 48. For example, as shown, the end of each leaf 25 may be shaped to define an orifice 48, and each wire may pass through the respective orifices of two adjacent leaves, such that the wire forms a loop that passes through the orifices. (Thus, as shown, a shunt having six proximal leaves is coupled to three wires 36, each wire separately controlling the collapse of a respective pair of adjacent leaves.) To collapse the proximal portion of the shunt, the two proximal ends of each of the wires are pulled, as described below with reference to FIG. 3A.

Alternatively to the embodiment shown, a single wire 36 may form a loop that passes through all of the orifices, this single wire controlling the collapse of the entire proximal portion. (In other words, by pulling on the two ends of this single wire, the entire proximal portion may be collapsed.) In yet other embodiments, wires 36 do not form loops; rather, a separate wire is coupled to each leaf. For example, each leaf may be coupled to the distal end of a respective wire. (Thus, for example, a shunt having six proximal leaves is coupled to six wires, one wire per leaf.) Similarly, wires 36 may be formed as extensions of the leaves, such that each leaf has a wire extension that extends to the exterior of the subject. In such embodiments, the proximal portion of the shunt may be collapsed by pulling on the single proximal end of each of the wires.

In some cases, it may be beneficial to adjust the diameter of intermediate portion 42 while the shunt is inside the subject. Hence, apparatus 28 typically further comprises a constricting flexible longitudinal element that passes circumferentially along intermediate portion 42, and extends from the intermediate portion of the shunt to the exterior of the subject. For example, as shown, the constricting flexible longitudinal element may comprise a wire 38 that loops around the intermediate portion of the shunt, both ends of the wire passing through the vasculature of the subject (e.g., within lumen 37, or within a separate lumen 39 of sheath 31), exiting from the subject (e.g., via a femoral vein), and being coupled to control handle 34. The constricting flexible longitudinal element is configured to constrict the intermediate portion of the shunt, by exerting an inward radial force on the intermediate portion of the shunt. For example, to constrict the intermediate portion, and thus reduce the flow of blood across the septum, the control handle may be used to pull both ends of wire 38. (Subsequently, the control handle may be used to hold wire 38 in place, to prevent the intermediate portion from re-expanding.) Conversely, to widen the intermediate portion, the control handle may be used to release wire 38, thus allowing the intermediate portion to expand radially outward.

In some embodiments, as shown, the intermediate portion is shaped to define a plurality of orifices 50, and the wire passes circumferentially along the intermediate portion by passing through the orifices. Alternatively or additionally to comprising a wire, the constricting flexible longitudinal element may comprise a band, strap, ribbon, or any other suitable type of longitudinal element.

In some embodiments, the adjustment of the diameter of the shunt is based on pressure monitoring. For example, as further described below, pressure sensors disposed on the shunt may be used to acquire intra-atrial pressure measurements, and the diameter of the shunt may be adjusted in response to such measurements. Alternatively or additionally, the diameter of the shunt may be adjusted in response to hemodynamic monitoring, such as by the application of flow imaging techniques such as pulsed wave (PW) or continuous wave (CW) Doppler echocardiography.

Typically, to place the shunt within the septum, the shunt is first collapsed and placed inside a delivery catheter 46. Subsequently, catheter 46 is percutaneously inserted into the vasculature of the subject, such as via a femoral vein of the subject, and is then passed through the vasculature into right atrium 30, e.g., via the inferior vena cava. (Alternatively, catheter 46 may be passed into the right atrium via the jugular vein and superior vena cava.) Subsequently, the distal end of the catheter is passed through the septum and into left atrium 32, such that the distal and proximal portions of the shunt are on opposite sides of the septum. (As is known in the art, prior to passing the distal end of the catheter through the septum, a puncturing element may be used to create an opening in the septum, and, optionally, a dilator may be used to enlarge the opening, such that the distal end of the catheter may easily pass through the septum.) The catheter is then withdrawn from over the shunt while the shunt is held in place. As the catheter is withdrawn from over the shunt, the shunt reassumes its natural, non-collapsed shape, such that distal portion 40 opens on the left-atrium side of the septum, and proximal portion 44 opens on the right-atrium side of the septum.

Following the deployment of the shunt, the catheter is withdrawn from the subject, leaving behind the shunt, along with the shunt-collapsing flexible longitudinal elements and the constricting flexible longitudinal element. Alternatively, the catheter may remain within the subject while the shunt is in place. For example, the catheter may remain within the subject such that the distal end of the catheter is near the proximal portion of the shunt. The catheter may thus be used to deliver medication to the shunt site, and/or pressure sensors in the catheter may be used to monitor the intra-atrial pressure.

By way of example, FIG. 1 shows the catheter coupled to a control handle 34, such that control handle 34 may be used to advance and withdraw the catheter. (FIG. 1 shows a scenario in which the catheter has been withdrawn from within the subject, but remains coupled to the control handle, poised for reentry into the subject.)

Shunt 26 helps relieve excess intra-atrial pressure, by allowing blood to flow from the higher-pressure atrium to the lower-pressure atrium. Shunt 26 may thus be used to treat any relevant condition (e.g., pulmonary hypertension or congestive heart failure) for which the relief of excess pressure is beneficial, or, for example, to help prevent left ventricular dilation and remodeling following an acute myocardial insult. Typically, the subject remains hospitalized until the subject's physician decides that sufficient treatment has been provided, at which point the shunt is removed from the subject (as further described immediately below), and the subject is released from hospital. In some embodiments, shunt apparatus 28 comprises one or more pressure sensors, disposed, for example, on shunt 26, on any of the longitudinal elements, and/or in sheath 31. Such pressure sensors may be used to measure (e.g., continuously) the pressure in the subject's right atrium and/or left atrium, in order to monitor progression of the treatment, and ascertain the point in time at which the shunt may be removed from the subject. For example, one pressure sensor may be disposed on the proximal portion of the shunt, and another pressure sensor on the distal portion of the shunt, such that the pressure in both the left atrium and the right atrium is measured.

Figure 3C:
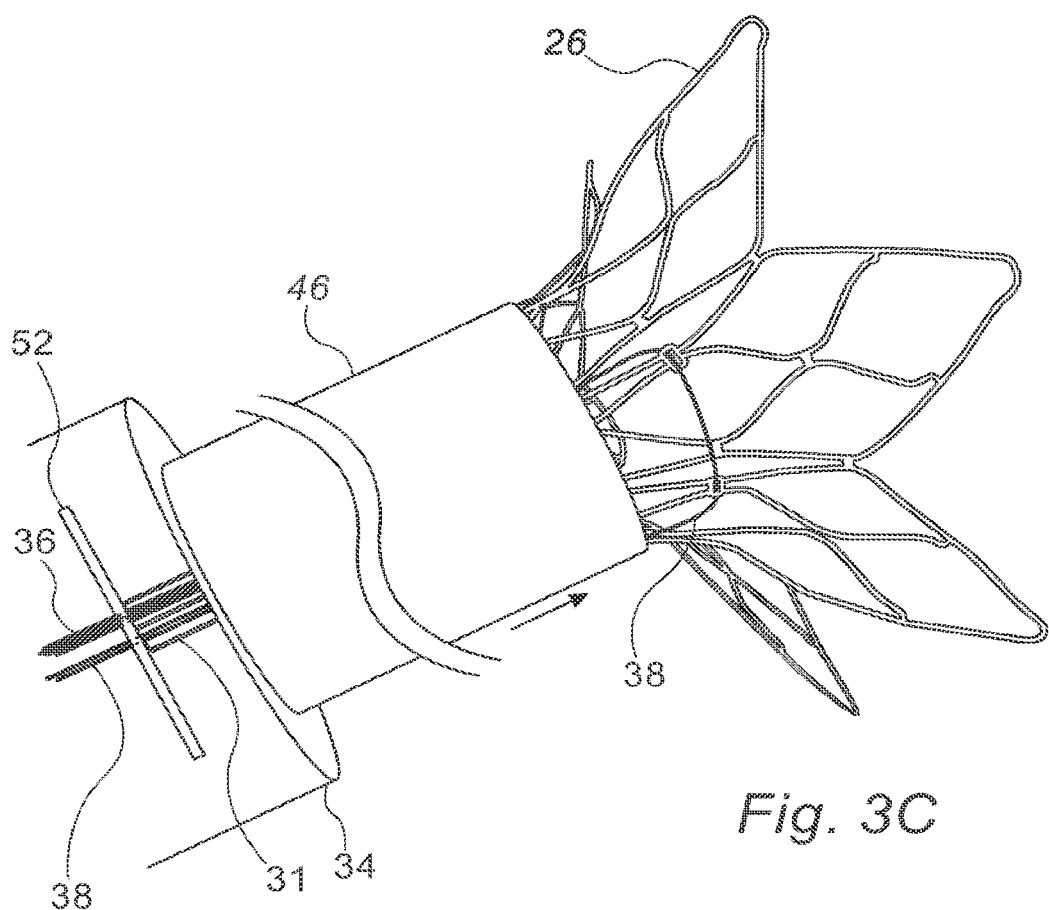

Reference is now made to FIGS. 3A-C, which collectively show a technique for removing shunt 26 from subject 20, in accordance with some embodiments of the present invention. It is noted that many of the details shown in FIGS. 3A-C are provided by way of example only, and that many variations of the illustrated technique are included within the scope of the present disclosure.

In FIG. 3A, catheter 46 is reinserted into the subject, and is then advanced until the distal end of the catheter is close to proximal portion 44 of the shunt. Subsequently, wires 36 are pulled, as indicated by the arrow 54 shown in the figure, such that an inward radial force is exerted on proximal portion 44. The inward radial force causes proximal portion 44 to collapse, as shown in FIG. 3B. Following the collapse of the proximal portion of the shunt, as shown in FIG. 3C, the catheter is advanced distally over the shunt. (In passing over the shunt, the catheter may at least partly pass through the interatrial septum.) As the catheter continues to pass over the shunt from the position shown in FIG. 3C, the catheter collapses the distal end of the shunt, such that the shunt becomes entirely collapsed within the catheter. Subsequently, the catheter, containing the shunt, may be removed from the subject.

In some embodiments, the catheter is advanced while proximal portion 44 is collapsing, such that, as proximal portion 44 continues to collapse, the catheter passes over the shunt, until the distal end of the catheter crosses through the septum and reaches the distal portion of the shunt. (In such embodiments, the state shown in FIG. 3B does not actually come to transpire, since catheter 46 covers the proximal portion of the shunt before the proximal portion of the shunt is fully collapsed.) Then, as the pulling of wires 36 continues while the catheter is held in place or is pushed forward, the distal end of the catheter exerts a force on the distal portion of the shunt, such that the distal portion of the shunt collapses, and the shunt is drawn into the catheter. Such embodiments have the advantage that, due to the catheter being advanced over the shunt while wires 36 are pulled, the shunt is less likely to be pulled into the right atrium.

FIGS. 3A-C show, by way of example, an embodiment in which sheath 31 extends to a stopper 52 contained inside of control handle 34, wires 36 passing through stopper 52. As the wires are pulled, stopper 52 prevents sheath 31 from moving proximally, such that most of the pulling force acts on proximal portion 44, rather than on sheath 31. (Although flexible, sheath 31 is resistant to buckling, such that the pulling force is effectively transferred to proximal portion 44.) A similar mechanism may be used for wire 38, which, as described above, controls the diameter of the intermediate portion of the shunt. (In the context of the present application, including the claims, the term "stopper" may refer to anything that stops something else. For example, stopper 52 is referred to as a "stopper," in that it stops the proximal movement of sheath 31.)

In some embodiments, two separate tubes run through a single lumen, or two separate lumens, of sheath 31, one of these tubes holding wires 36, and the other of these tubes holding wire 38. Such tubes—which may comprise, for example, HHS® ("Helical Hollow Strand") Tubes—may provide additional resistance to buckling, such that the pulling force exerted on the wires is effectively transmitted to the shunt. In such embodiments, stopper 52 may be used to prevent the wire-holding tubes from moving proximally as the wires are pulled.

It is noted that the apparatus and methods described above may also be used for applications in which an implanted shunt is required. In such applications, during the implantation procedure, wires 36 may be used to facilitate the retrieval of shunt 26, in the event that the shunt was riot placed at the proper location. Subsequently, upon confirmation that the shunt is properly situated, wires 36 may be detached from shunt 26, and removed from the subject. Similarly, during the implantation procedure, the constricting flexible longitudinal element may be used to adjust the diameter of the shunt. Subsequently, upon completion of the adjustment, the constricting flexible longitudinal element may be locked in place, such as to maintain the diameter of the shunt, and then any proximally-extending portion of the constricting flexible longitudinal element may be detached and removed.

Figure 4A:
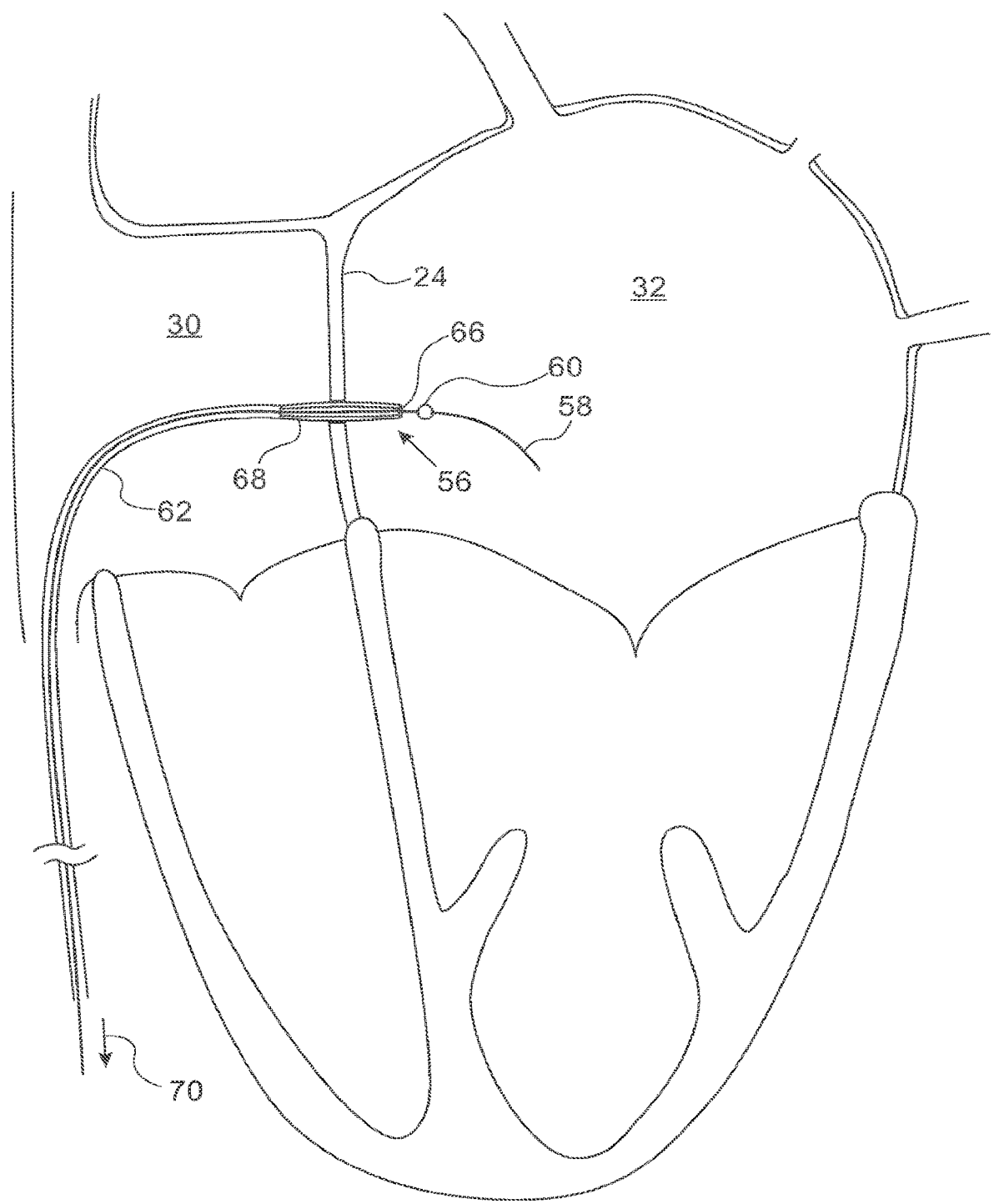
FIGS. 4A-B are schematic illustrations showing the placement of a temporary shunt within an interatrial septum, in accordance with some embodiments of the present invention.
Figure 4B:
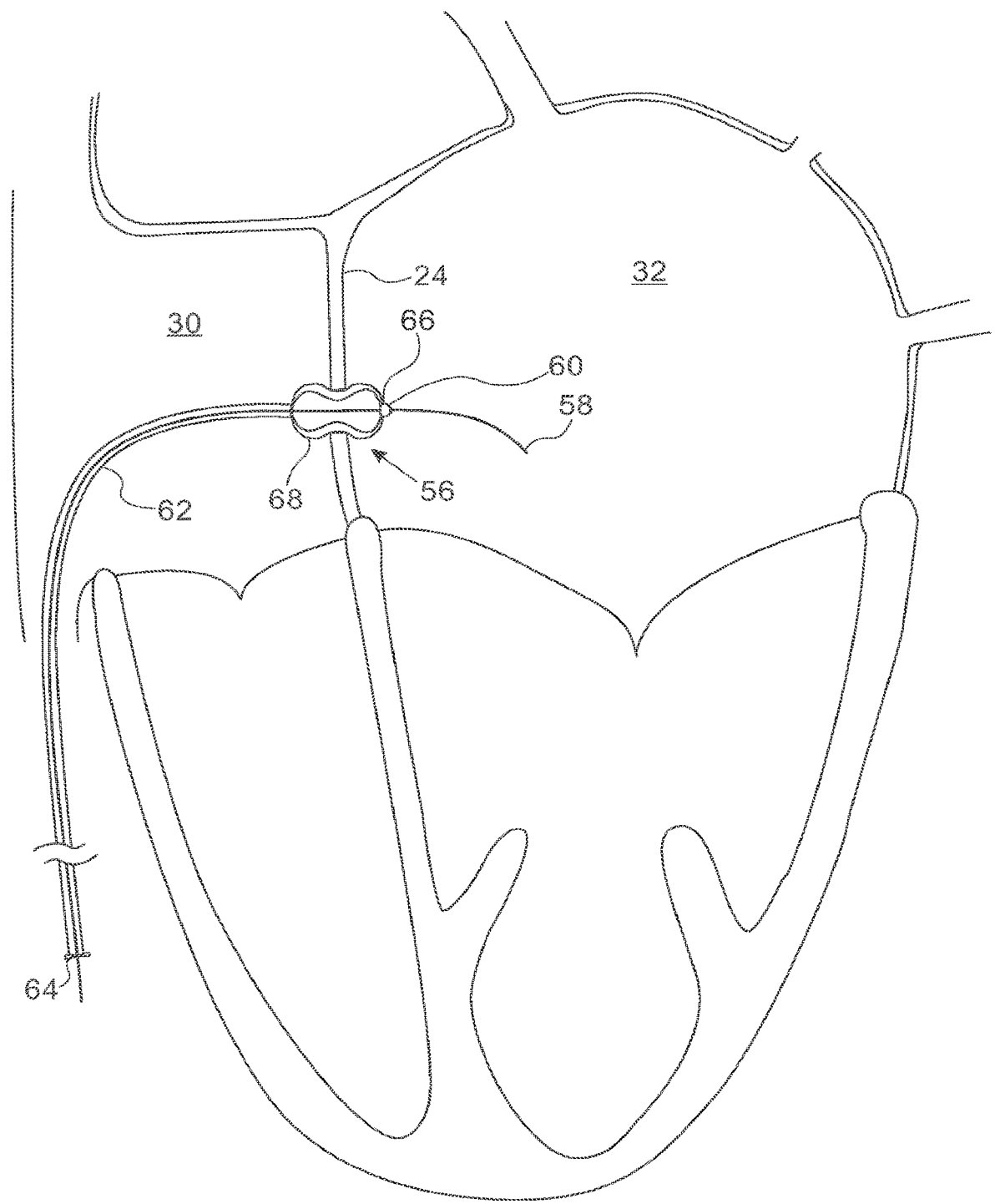

Reference is now made to FIGS. 4A-B, which are schematic illustrations showing the placement of a temporary shunt 56 within interatrial septum 24, in accordance with some embodiments of the present invention. Apparatus and methods described with reference to FIGS. 4A-B may be used for applications in which temporary shunting is desired, alternatively to apparatus and methods described with reference to earlier figures. Thus, for example, as described above for shunt 26, shunt 56 may be removed less than one week from placement of the shunt.

Typically, shunt 56 is an expandable structure made from a suitable shape-memory material, such as Nitinol, such that shunt 56 may move from a collapsed state (shown in FIG. 4A) to a preconfigured open state (shown in FIG. 4B) upon being subjected to an appropriate force, and may then recollapse upon removal of the force. In general, shunt 56 may have any suitable form. For example, as shown in the figures, shunt 56 may comprise a plurality of wires 68, which are joined together at their distal ends (e.g., by being connected to a common ring), and are coupled to a sheath 62 at their proximal ends. (Sheath 62 may be referred to as a "subselective sheath," in that the diameter of sheath 62 is small, relative to the "vascular sheath" referred to below.) In the collapsed state of the shunt, wires 68 are approximately parallel to each other along the majority of the length of the wires. Upon the distal and proximal ends of the wires being pushed together (i.e., upon the shunt being longitudinally compressed), the wires expand radially outward from each other, such that the shunt assumes the preconfigured open state. Typically, in the shunt's preconfigured open state, the proximal portion of the shunt and the distal portion of the shunt are wider than the intermediate portion of the shunt that is between the proximal portion of the shunt and the distal portion of the shunt. The wider proximal and distal portions of the shunt anchor the shunt to the septum (i.e., prevent migration of the shunt front within the septum).

As described above with respect to shunt 26, shunt 56 is percutaneously inserted into the subject. First, a guidewire 58 is inserted into the right atrium, e.g., via the femoral vein and the inferior vena cava, as shown. Subsequently, guidewire 58 is passed across septum 24 (from the right atrium to the left atrium), using conventional techniques known in the art, such that the distal portion of the guidewire is in the left atrium. (To introduce guidewire 58, a vascular sheath (not shown), which may alternatively be referred to as a catheter, may be used, as is known in the art. If necessary, a dilating tool may be passed over the guidewire, and through the opening created by the guidewire, to enlarge the opening in the septum.) Subsequently to passing the guidewire across the septum, shunt 56 is passed, in a collapsed state, over the guidewire, until the distal portion of the shunt is in the left atrium, and the proximal portion of the shunt is in the right atrium. In other words, as shown in FIG. 4A, shunt 56 is positioned over the guidewire such that the shunt spans the septum.

A stopper 60 is coupled to the distal portion of guidewire 58 (i.e., near the distal end of the guidewire, such as within one or two millimeters of the distal end). Subsequently to positioning the shunt such that the shunt spans the septum, the stopper is used to open the shunt from the shunt's initial collapsed state. In one embodiment of this technique, the guidewire is retracted (proximally pulled), as indicated by the arrow 70 in the figure, such that the stopper presses against the distal portion of the shunt. While the guidewire is retracted, sheath 62 (and hence, the proximal end of the shunt) is held in place or is advanced, such that, by pressing against the distal portion of the shunt, the stopper applies a longitudinally compressive force to the shunt. The compressive force causes the shunt to open, and hence, the opening in the septum to become enlarged, as shown in FIG. 4B. (In alternative embodiments, the stopper may press against the distal portion of the shunt by virtue of the sheath being advanced while the guidewire is held in place.)

Stopper 60 is referred to herein as a "stopper," in that stopper 60 stops the advancement of the shunt along the guidewire, by virtue of the stopper being large enough such that the shunt cannot pass over the stopper. Stopper 60 may have any form suitable for applying the longitudinally compressive force to the shunt. For example, the stopper may comprise a bead, as shown in the figure; alternatively, for example, stopper 60 may comprise a plate or rod which, when pressed against the shunt, applies the longitudinally compressive force. In some embodiments, the shunt is shaped to define a distal aperture 66, shaped to fittingly receive the stopper. (In such embodiments, the stopper may be referred to as a "lock," and distal aperture 66 may be referred to as a "fitting.") As the guidewire is withdrawn in the proximal direction, the stopper engages with, i.e., is fittingly received by, distal aperture 66. Subsequently, the stopper continues to press against the distal portion of the shunt while the stopper is fittingly received by the distal aperture. The engagement between the distal aperture and the stopper helps the pressing force to be more effectively applied to the shunt.

Typically, to maintain the open state of shunt 56, it is necessary to maintain the longitudinally compressive force on the shunt. This may be accomplished by, using a locking mechanism, locking sheath 62 with respect to (or "against") the guidewire, i.e., fixing the position of the sheath with respect to the guidewire. For example, FIG. 4B shows a lock 64 placed over the guidewire, proximally to the sheath. Lock 64 prevents the sheath from sliding backward along the guidewire, and the guidewire from sliding forward within the sheath, such that the longitudinally compressive force on the shunt is maintained. In some embodiments, the guidewire and sheath are coupled to control handle 34 (FIG. 1), and the control handle is used to lock the sheath.

Subsequently, upon completion of the treatment, the sheath is unlocked, e.g., by removing lock 64. The unlocking of the sheath allows the sheath to move proximally, and/or allows the guidewire to move distally, thus removing the longitudinally compressive force that had heretofore been applied to the shunt. The shunt therefore collapses. Subsequently, the sheath, and the shunt, are removed from the subject.

In some embodiments, prior to unlocking the sheath, a catheter is advanced over the sheath, until the distal end of the catheter is near the proximal end of the shunt. Subsequently, upon collapse of the shunt, the shunt is pulled into the catheter, and/or the catheter is advanced over the shunt. The catheter is then used to remove the shunt from the subject. In other embodiments, no catheter is used for removal of the shunt. Rather, upon collapse of the shunt, the sheath and shunt are proximally pulled, through the vasculature of the subject, out of the subject.

In some embodiments, one or more pressure sensors are disposed on guidewire 58, shunt 56, and/or sheath 62. Such pressure sensors may be used to measure the pressure in the subject's right atrium and/or left atrium, as described above for apparatus 28.

Although the description above relates mainly to interatrial shunting, it is noted that shunt 56, and the above-described techniques for deployment thereof, may be used for shunting between any relevant two body cavities. For example, in an interventricular shunting application, guidewire 58 may be passed through the interventricular septum, from the right ventricle to the left ventricle, and the shunt may then be deployed over the guidewire and opened within the interventricular septum.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
   placing a shunt across an aperture in an atrial septum of a subject, such that one or more retrieval elements extend from a proximal portion of the shunt to a catheter;
   transitioning the shunt from a collapsed delivery state to an expanded deployed state such that an intermediate portion of the shunt is positioned in the aperture in the atrial septum; and
   subsequently, using the one or more retrieval elements, collapsing the shunt,
   wherein the one or more retrieval elements remain coupled to the shunt throughout the time the shunt is placed inside the subject.

2. The method according to claim 1, further comprising, using the catheter, removing the shunt from the subject.

3. The method according to claim 2, wherein removing the shunt from the subject comprises removing the shunt from the subject after less than one week from the placement of the shunt.

4. The method according to claim 1, further comprising creating the aperture in the atrial septum of the patient using a puncturing device.

5. The method according to claim 1, further comprising advancing a guidewire across the aperture in the atrial septum of the patient, and wherein placing the shunt across the aperture in the atrial septum comprises placing the shunt across the aperture in the atrial septum over the guidewire.

6. The method according to claim 1, further comprising constricting the intermediate portion of the shunt using a constricting flexible longitudinal element that extends from the catheter and passes circumferentially along the intermediate portion of the shunt.

7. The method according to claim 6, further comprising:
   measuring an intra-atrial pressure of the subject; and
   adjusting a diameter of the shunt by constricting the intermediate portion of the shunt using the constricting flexible longitudinal element based on the measured intra-atrial pressure.

8. The method according to claim 6, wherein constricting the intermediate portion of the shunt using the constricting flexible longitudinal element comprises passing the constricting flexible longitudinal element through a bead.

9. The method according to claim 6, further comprising:
   measuring hemodynamics of the subject; and
   adjusting a diameter of the shunt by constricting the intermediate portion of the shunt using the constricting flexible longitudinal element based on the measured hemodynamics.

10. The method according to claim 6, wherein the intermediate portion of the shunt comprises a plurality of orifices such that the constricting flexible longitudinal element passes circumferentially along the intermediate portion of the shunt through the plurality of orifices.

11. The method according to claim 6, further comprising enlarging the intermediate portion of the shunt using the constricting flexible longitudinal element.

12. The method according to claim 11, wherein enlarging the intermediate portion of the shunt comprises controllably releasing the constricting flexible longitudinal element to permit the intermediate portion of the shunt to expand radially outward.

13. The method according to claim 1, wherein transitioning the shunt from the collapsed delivery state to the expanded deployed state comprises retracting a sheath from over the shunt while the shunt is positioned across the aperture in the atrial septum.

14. The method according to claim 13, further comprising advancing the sheath over the one or more retrieval elements of the shunt to collapse the proximal portion of the shunt.

15. The method according to claim 14, further comprising advancing the sheath over the shunt until a distal end of the sheath reaches a distal portion of the shunt to fully collapse the shunt.

16. The method according to claim 1, wherein, in the expanded deployed state, the proximal portion of the shunt and a distal portion of the shunt are wider than the intermediate portion of the shunt.

17. The method according to claim 5, further comprising enlarging the aperture in the atrial septum using a dilator.

18. The method according to claim 1, further comprising shunting blood through a passageway of the shunt across the atrial septum in the expanded deployed state.

19. The method according to claim 1, wherein the shunt and the one or more retrieval elements comprise a plurality of wires with proximal ends coupled to the catheter.

20. The method according to claim 19, wherein transitioning the shunt from the collapsed delivery state to the expanded deployed comprises expanding the plurality of wires radially outward from each other.

\* \* \* \* \*